(12) United States Patent
Cartledge et al.

(10) Patent No.: US 12,329,630 B2
(45) Date of Patent: *Jun. 17, 2025

(54) SURGICAL IMPLANT DEVICES AND METHODS FOR THEIR MANUFACTURE AND USE

(71) Applicant: Edwards Lifesciences CardiAQ LLC, Irvine, CA (US)

(72) Inventors: Richard George Cartledge, Boca Raton, FL (US); John P. Cartledge, Boca Raton, FL (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 18/086,059

(22) Filed: Dec. 21, 2022

(65) Prior Publication Data

US 2023/0128901 A1    Apr. 27, 2023

Related U.S. Application Data

(63) Continuation of application No. 16/716,416, filed on Dec. 16, 2019, now Pat. No. 11,540,911, which is a
(Continued)

(51) Int. Cl.
*A61F 2/07*    (2013.01)
*A61F 2/06*    (2013.01)
(Continued)

(52) U.S. Cl.
CPC ............... *A61F 2/07* (2013.01); *A61F 2/064* (2013.01); *A61F 2/966* (2013.01);
(Continued)

(58) Field of Classification Search
CPC .. A61F 2/07; A61F 2/966; A61F 2/064; A61F 2002/9534; A61F 2250/0098
See application file for complete search history.

(56) References Cited

U.S. PATENT DOCUMENTS 3,409,013 A    11/1968 Berry
3,548,417 A    12/1970 Ronnie et al.
(Continued)

FOREIGN PATENT DOCUMENTS

DE    0144167 C    9/1903
DE    2246526 A1   3/1973
(Continued)

OTHER PUBLICATIONS

H.R. Andersen, et al. "Transluminal Implantation of Artificial Heart Valve. Description of a New Expandable Aortic Valve and Intitial Results with implantation by Catheter Tehnique in Closed Chest Pig," European Heart Journal, No. 13. pp. 704-708. 1992.
(Continued)

*Primary Examiner* — Diane D Yabut
(74) *Attorney, Agent, or Firm* — Klarquist Sparkman, LLP; Joel B. German

(57) ABSTRACT

An assembly includes an implant body and a delivery apparatus. The implant body includes a lattice structure, an adjustment member, and a control device. The lattice structure is circumferentially expandable and contractible. The adjustment member and the control device are coupled to the lattice structure. Actuating the adjustment member results in circumferential expansion or contraction of the lattice structure. The delivery apparatus includes a rotatable adjustment tool and a locking mechanism comprising a controllable catch coupled to an end portion of the rotatable adjustment tool. The rotatable adjustment tool is configured to actuate the adjustment member of the implant body upon rotation of the rotatable adjustment tool. The controllable catch of the locking mechanism is configured to selectively couple the rotatable adjustment tool to the adjustment member of the implant body.

18 Claims, 15 Drawing Sheets

Related U.S. Application Data continuation of application No. 15/448,417, filed on Mar. 2, 2017, now Pat. No. 10,507,097, which is a continuation of application No. 13/339,236, filed on Dec. 28, 2011, now Pat. No. 9,585,743.

(60) Provisional application No. 61/428,114, filed on Dec. 29, 2010.

(51) Int. Cl.
*A61F 2/966* (2013.01)
*A61F 2/89* (2013.01)
*A61F 2/95* (2013.01)

(52) U.S. Cl.
CPC .......... *A61F 2002/075* (2013.01); *A61F 2/89* (2013.01); *A61F 2002/9534* (2013.01); *A61F 2250/0001* (2013.01); *A61F 2250/0004* (2013.01); *A61F 2250/001* (2013.01); *A61F 2250/0069* (2013.01); *A61F 2250/0098* (2013.01)

(56) References Cited

U.S. PATENT DOCUMENTS

| | | |
|---|---|---|
| 3,587,115 A | 6/1971 | Donald |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |

(56) References Cited

U.S. PATENT DOCUMENTS

| | | |
|---|---|---|
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,647,378 B2 * | 2/2014 | Mews .............. A61B 17/885 623/1.11 |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 11,224,509 B2 | 1/2022 | Dasi et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |

(56) References Cited

U.S. PATENT DOCUMENTS

| | | |
|---|---|---|
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 1991017720 A1 | 11/1991 |
| WO | 1992017118 A1 | 10/1992 |
| WO | 1993001768 A1 | 2/1993 |
| WO | 1997024080 A1 | 7/1997 |
| WO | 1998029057 A1 | 7/1998 |
| WO | 1999030646 A1 | 6/1999 |
| WO | 1999033414 A1 | 7/1999 |
| WO | 1999040964 A1 | 8/1999 |
| WO | 1999047075 A1 | 9/1999 |
| WO | 2000018333 A1 | 4/2000 |
| WO | 2000041652 A1 | 7/2000 |
| WO | 2000047139 A1 | 8/2000 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001062189 A1 | 8/2001 |
| WO | 2001064137 A1 | 9/2001 |
| WO | 2001076510 A2 | 10/2001 |
| WO | 2002022054 A1 | 3/2002 |
| WO | 2002036048 A1 | 5/2002 |
| WO | 2002041789 A2 | 5/2002 |
| WO | 2002043620 A1 | 6/2002 |
| WO | 2002047575 A2 | 6/2002 |
| WO | 2002049540 A2 | 6/2002 |
| WO | 2003047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A1 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. Pp 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

\* cited by examiner

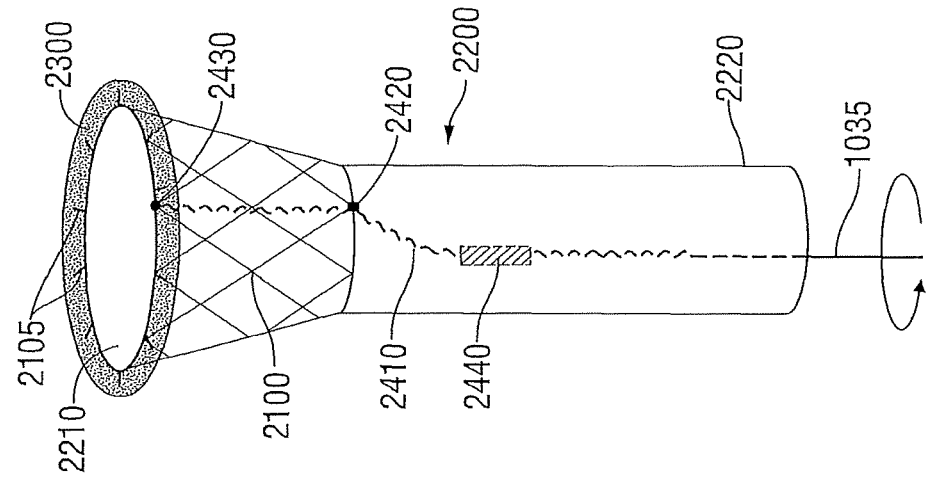
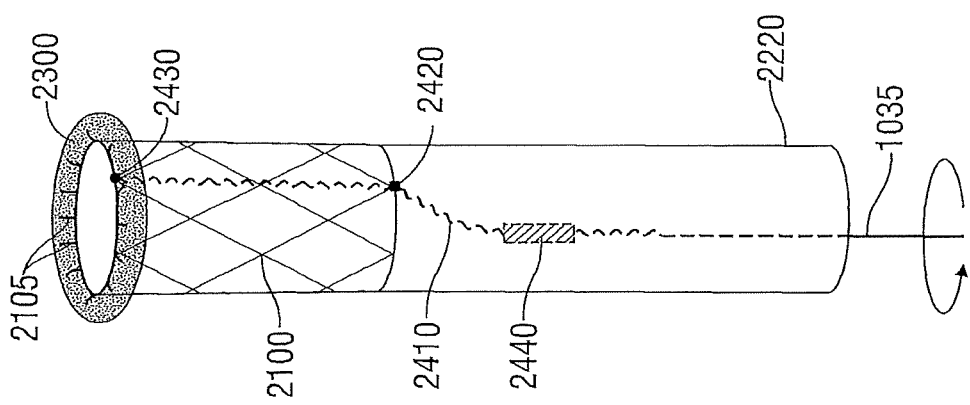

SURGICAL IMPLANT DEVICES AND METHODS FOR THEIR MANUFACTURE AND USE

CROSS-REFERENCE TO RELATED APPLICATIONS

This application is a continuation of U.S. patent application Ser. No. 16/716,416, filed on Dec. 16, 2019, which is a continuation of U.S. patent application Ser. No. 15/448,417, filed on Mar. 2, 2017, now U.S. Pat. No. 10,507,097, which is a continuation of U.S. patent application Ser. No. 13/339,236, filed Dec. 28, 2011, now U.S. Pat. No. 9,585,743, which claims the benefit of U.S. Provisional Patent Application No. 61/428,114, filed Dec. 29, 2010, all of which are incorporated by reference herein.

STATEMENT REGARDING FEDERALLY SPONSORED RESEARCH OR DEVELOPMENT

Not Applicable

FIELD OF THE INVENTION

The present invention relates to the field of surgical implant devices and methods for their manufacture and use. Among the exemplary embodiments of the present invention are improvements in sealing and retention medical devices particularly applicable to vascular surgery and the treatment of aneurysms or other luminal defects in other anatomic conduits, such as sealing and retention of replacement heart valves.

BACKGROUND OF THE INVENTION

Medical and surgical implants are placed often in anatomic spaces where it is desirable for the implant to conform to the unique anatomy of the targeted anatomic space and secure a seal therein, preferably without disturbing or distorting the unique anatomy of that targeted anatomic space.

While the lumens of most hollow anatomic spaces are ideally circular, in fact, the cross-sectional configurations of most anatomic spaces are, at best, ovoid, and may be highly irregular. Such lumenal irregularity may be due to anatomic variations and/or to pathologic conditions that may change the shape and topography of the lumen and its associated anatomic wall. Examples of anatomic spaces where such implants may be deployed include, but are not limited to, blood vessels, the heart, other vascular structures, vascular defects (such as thoracic and abdominal aortic aneurysms), the trachea, the oropharynx, the esophagus, the stomach, the duodenum, the ileum, the jejunum, the colon, the rectum, ureters, urethras, fallopian tubes, biliary ducts, pancreatic ducts, or other anatomic structures containing a lumen used for the transport of gases, blood, or other liquids or liquid suspensions within a mammalian body.

For a patient to be a candidate for existing endograft methods and technologies, to permit an adequate seal, a proximal neck of, ideally, at least 12 mm of normal aorta must exist downstream of the left subclavian artery for thoracic aortic aneurysms or between the origin of the most inferior renal artery and the origin of the aneurysm in the case of abdominal aneurysms. Similarly, ideally, at least 12 mm of normal vessel must exist distal to the distal extent of the aneurysm for an adequate seal to be achieved.

Migration of existing endografts has also been a significant clinical problem, potentially causing leakage and profusion of aneurysms and/or compromising necessary vascular supplies to arteries such as the carotid, subclavian, renal, or internal iliac vessels. This problem only has been addressed partially by some existing endograft designs, in which barbs or hooks have been incorporated to help retain the endograft at its intended site. However, most existing endograft designs are solely dependent on radial force applied by varying length of stent material to secure a seal against the recipient vessel walls.

Because of the limitations imposed by existing vascular endograft devices and endovascular techniques, a significant number of abdominal and thoracic aneurysms repaired in the U.S. are still managed though open vascular surgery, instead of the lower morbidity of the endovascular approach.

Pre-sizing is required currently in all prior art endografts. Such pre-sizing based on CAT-scan measurements is a significant problem. This leads, many times, to mis-sized grafts. In such situations, more grafts segments are required to be placed, can require emergency open surgery, and can lead to an unstable seal and/or migration. Currently there exists no endograft that can be fully repositioned after deployment.

Thus, a need exists to overcome the problems with the prior art systems, designs, and processes as discussed above.

SUMMARY OF THE INVENTION

The invention provides surgical implant devices and methods for their manufacture and use that overcome the hereinafore-mentioned disadvantages of the heretofore-known devices and methods of this general type and that provide such features with improvements that increase the ability of such an implant to be precisely positioned and sealed, with better in situ accommodation to the local anatomy of the targeted anatomic site. The invention provide an adjustment tool that can remotely actuate an adjustment member(s) that causes a configuration change of a portion(s) of an implant, which configuration change includes but is not limited to diameter, perimeter, shape, and/or geometry or a combination of these, to create a seal and provide retention of an implant to a specific area of a target vessel or structure.

One exemplary aspect of the present invention is directed towards novel designs for endovascular implant grafts, and methods for their use for the treatment of aortic aneurysms and other structural vascular defects. An endograft system for placement in an anatomic structure or blood vessel is disclosed in which an endograft implant comprises, for example, a non-elastic tubular implant body with at least an accommodating proximal end. Accommodating, as used herein, is the ability to vary a configuration in one or more ways, which can include elasticity, expansion, contraction, and changes in geometry. Both or either of the proximal and distal ends in an implant according to the present invention further comprise one or more circumferential expandable sealable collars and one or more expandable sealing devices, capable of being expanded upon deployment to achieve the desired seal between the collar and the vessel's inner wall. Exemplary embodiments of such devices can be found in co-pending U.S. patent application Ser. Nos. 11/888,009, filed Jul. 31, 2007, and Ser. No. 12/822,291, filed Jun. 24, 2010, which applications have been incorporated herein in their entireties. Further embodiments of endovascular implants according to the present invention may be provided with retractable retention tines or other retention devices allowing an implant to be repositioned before final deployment. In other embodiments, the implant can be repositioned after final deployment. An endograft system according to the present invention further comprises a delivery catheter with an operable tubular sheath capable of housing a folded or compressed endograft implant prior to deployment and capable of retracting or otherwise opening in at least its proximal end to allow implant deployment. The sheath is sized and configured to allow its placement via a peripheral arteriotomy site, and is of appropriate length to allow its advancement into the aortic valve annulus, ascending aorta, aortic arch, and thoracic or abdominal aorta, as required for a specific application.

While some post-implantation remodeling of the aortic neck proximal to an endovascular graft (endograft) has been reported, existing endograft technology does not allow for the management of this condition without placement of an additional endograft sleeve to cover the remodeled segment.

Exemplary endografts of the present invention as described herein allow for better accommodation by the implant of the local anatomy, using a self-expandable or compressible gasket for the sealing interface between the endograft collar and the recipient vessel's inner wall. Furthermore, exemplary endografts of the present invention as disclosed herein are provided with a controllably releasable disconnect mechanism that allows remote removal of an adjustment tool and locking of the retained sealable mechanism after satisfactory positioning and sealing of the endograft. In some exemplary embodiments according to the present invention, the controllably releasable disconnect mechanism may be provided in a manner that allows post-implantation re-docking of an adjustment member to permit post-implantation repositioning and/or resealing of an endograft subsequent to its initial deployment.

In other exemplary applications encompassed by the present invention, improved devices for sealing other medical devices such as vascular cannulae may be provided. The present invention further includes novel designs for vascular cannulae to be used when bi-caval cannulation of the heart is indicated, eliminating the need to perform circumferential caval dissection and further reducing the tissue trauma caused by prior art balloon or other bypass cannulae. While the vascular cannulae of the present invention are inserted and positioned by a surgeon in the standard fashion, the need for circumferential dissection of the cavae and tourniquet placement is obviated. After the vascular cannulae of the present invention are positioned and secured with purse string sutures, the surgeon deploys the adjustable sealing devices of the cannulae by turning an adjustment tool or torque wire. Once the sealing devices are deployed, all of the venous return is diverted. The sealing devices deploy around the distal ends of the cannulae and allow blood to flow through the lumen of the cannulae, but not around the sealing devices. Use of these cannulae minimizes the chance of caval injury by eliminating the need for circumferential dissection. Additionally, the configuration of the adjustable sealing device in relation to the cannula is such that the adjustable sealing device is "flush" with the cannula so that no acute change in diameter exists along the external surface of the cannula, which serves to avoid tissue trauma during insertion and withdrawal into and out of bodily structures.

The present invention addresses several major problems presented by existing designs for balloon cannulae. In various exemplary embodiments according to the present invention, the lumens are configured such that a cannula with an adjustable sealing device can be deployed without compromising either the flow within the principle lumen of the cannula or the seal between the cannula and the structure within which the cannula lies. Moreover, a disclosed example of a cannula according to the present invention is provided with a trough within the cannula body at its distal end in which the adjustable sealing device member lies such that, when undeployed during insertion and withdrawal, there is a smooth interface between the external cannula wall and the undeployed sealing device, allowing for smoother, easier, and safer insertion and withdrawal.

Moreover, existing designs for balloon cannulae are unable to provide a truly symmetrical placement of an inflated balloon around a central lumen of standard diameter. The asymmetry that results with conventional balloon inflation is sufficient to displace the lumen from the true center of the endovascular lumen in which the balloon cannula is placed, resulting in unpredictable and suboptimal flow characteristics therethrough. The altered hemodynamics of such flow with an existing balloon cannula increases the likelihood of intimal vascular injury and clot or plaque embolization. Vascular cannulae of the present invention achieve the surprising result of having the flow characteristics of a non-balloon cannula by maintaining the preferred laminar flow characteristics of a circular main lumen of consistent diameter, positioned and maintained in or near the center of vascular flow by an adjustable sealing device originally provided within a recessed trough in the exterior wall of the cannula, with accessory lumens contained within an externally circular cannular wall. This allows for better seal, less vascular trauma, and easier vascular ingress and egress.

In addition, vascular cannulae according to the present invention may be provided with retractable stabilizing elements to anchor the inflated balloon within a vessel lumen during use. Such stabilizing elements further make use of the trough within the cannula body, with the stabilizing elements retracting into this trough during insertion and removal, allowing for smooth and trauma-free entry and egress of the cannula.

Certain aspects of the present invention are directed towards novel designs for sealable endovascular implant grafts, and methods for their use for the treatment of aortic aneurysms and other structural vascular defects or for heart valve replacements. Various embodiments as contemplated within the present invention may include any combination of exemplary elements as disclosed herein or in the co-pending patent applications referenced above.

In an exemplary embodiment according to the present invention, a sealable vascular endograft system for placement in a vascular defect is provided, comprising an elongated main implant delivery catheter with an external end and an internal end for placement in a blood vessel with internal walls. In such an exemplary embodiment, the main implant delivery catheter further comprises a main implant delivery catheter sheath that may be openable or removable at the internal end and a main implant delivery catheter lumen containing within a compressed or folded endovascular implant. Further, in such an exemplary embodiment, an endovascular implant comprises a non-elastic tubular implant body with an accommodating proximal end terminating in a proximal sealable circumferential collar that may be expanded by the operator to achieve a fluid-tight seal between the proximal sealable circumferential collar and the internal walls of the blood vessel proximal to the vascular defect. Moreover, in such an exemplary embodiment, an endovascular implant may further comprises a non-elastic tubular implant body with an accommodating distal end terminating in a distal sealable circumferential collar controlled by a distal variable sealing device, which may be expanded by the operator to achieve a fluid-tight seal between the distal sealable circumferential collar and the internal walls of the blood vessel distal to the vascular defect.

In a further exemplary embodiment according to the present invention, an implant interface is provided for a sealable attachment of an implant to a wall within the lumen of a blood vessel or other anatomic conduit.

In a yet further exemplary embodiment according to the present invention, an implant gasket interface is provided for a sealable attachment of an implant to a wall within the lumen of a blood vessel or other anatomic conduit, wherein the sealable attachment provides for auto-adjustment of the seal while maintaining wall attachment to accommodate post-implantation wall remodeling.

Still other exemplary embodiments of endografts and endograft delivery systems according to the present invention serve as universal endograft cuffs, being first placed to offer their advantageous anatomic accommodation capabilities, and then serving as a recipient vessel for other endografts, including conventional endografts.

Furthermore, exemplary embodiments of endografts and endograft delivery systems according to the present invention may be provided with a mechanism to permit transfer of torque or other energy from a remote operator to an adjustment member comprising a sealable, adjustable circumferential assembly controlled by an adjustment tool, which may be detachable therefrom and may further cause the assembly to lock upon detachment of the tool. In some exemplary embodiments of the present invention, the variable sealing device may be provided with a re-docking element that may be recaptured by subsequent operator interaction, allowing redocking and repositioning and/or resealing of the endograft at a time after its initial deployment.

Moreover, the various exemplary embodiments of the present invention as disclosed herein may constitute complete endograft systems, or they may be used as components of a universal endograft system as disclosed in co-pending patent applications that may allow the benefits of the present invention to be combined with the ability to receive other endografts.

Finally, the present invention encompasses sealable devices that may be used in other medical devices such as adjustable vascular cannulas or other medical or surgical devices or implants, such as aortic valves.

With the foregoing and other objects in view, there is provided, in accordance with the invention, a surgical implant including an implant body and a selectively adjustable assembly attached to the implant body, having adjustable elements, and operable to cause a configuration change in a portion of the implant body and, thereby, permit implantation of the implant body within an anatomic orifice to effect a seal therein under normal physiological conditions.

The preceding description is presented only as an exemplary application of the devices and methods according to the present invention.

Although the invention is illustrated and described herein as embodied in surgical implant devices and methods for their manufacture and use, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which:

FIG. 14A is a fragmentary, perspective view of an exemplary embodiment of an actively controllable endograft according to the present invention in which a latticework external to the lumen of an endograft can be radially displaced by controlled rotation of an adjustment member, the lattice structure being in a contracted state;

FIG. 14B is a fragmentary, perspective view of the actively controllable endograft of FIG. 14A in which the lattice structure is in an expanded state;

DETAILED DESCRIPTION OF THE INVENTION

Figure 2:
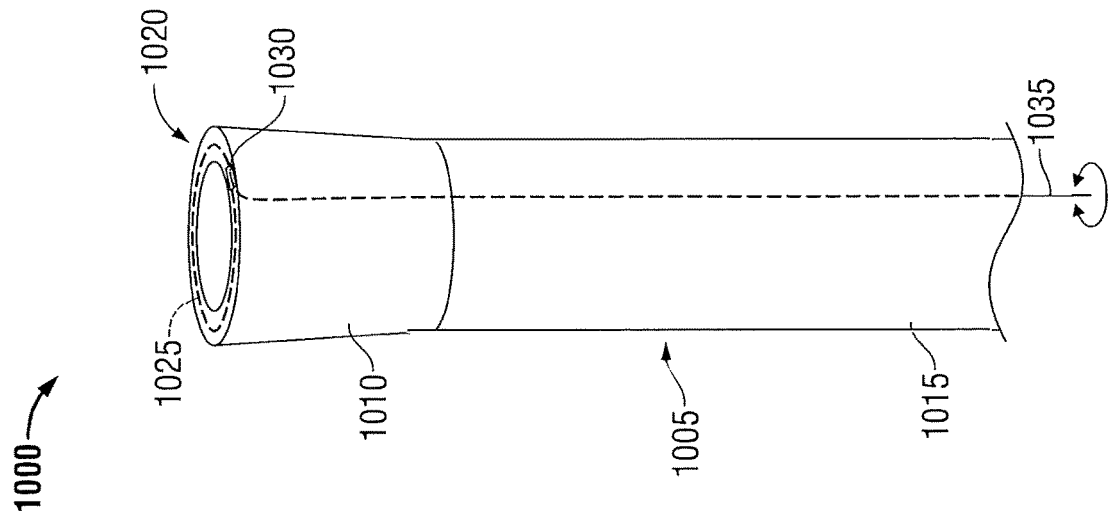
FIG. 2 is a fragmentary, perspective view of the selectively expandable and contractable endograft of FIG. 1 with the endograft in a relatively contracted form.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 1:
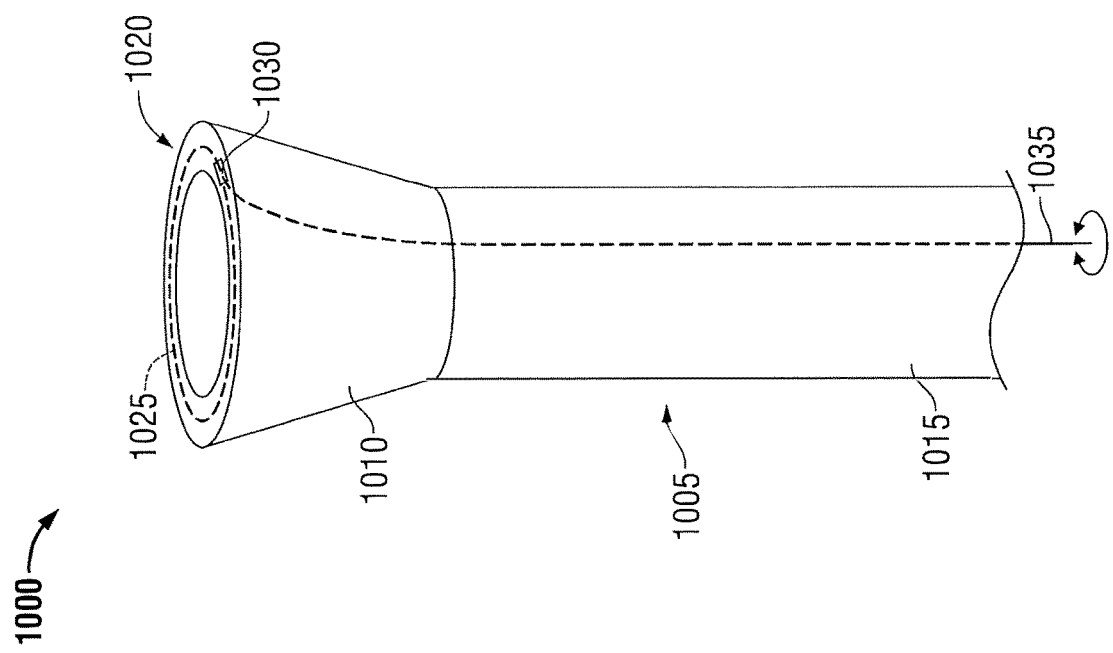
FIG. 1 is a fragmentary, perspective view of an exemplary embodiment of a proximal aspect of a selectively expandable and contractable endograft according to the present invention with the endograft in a relatively expanded form.
Figure 3:
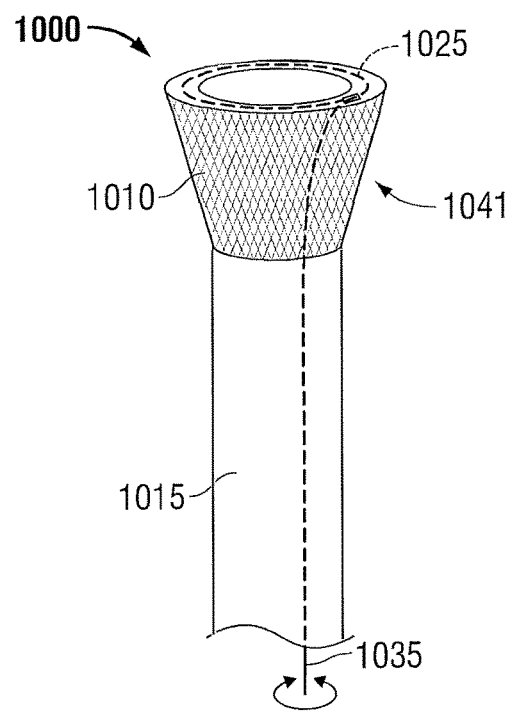
FIG. 3 is a fragmentary, perspective view of another exemplary embodiment of a proximal aspect of an endograft according to the present invention further incorporating a lattice structure.

Described now are exemplary embodiments of the present invention. Referring now to the figures of the drawings in detail and, first, particularly to FIG. 1 thereof, there is shown a perspective view of an exemplary embodiment of the proximal aspect of a sealable endograft system 1000 according to the present invention, in which the endograft is in a relatively expanded form. FIG. 2 is a perspective view of the embodiment of the proximal aspect of a sealable endograft system 1000 according to the present invention of FIG. 1, showing the endograft in a relatively contracted form. This exemplary endograft system 1000 has the ability to be selectively expanded and contracted to a diameter selected by the implanting physician. In general, the endograft system 1000 has, along its intermediate extent and, possibly, also at its distal portion (at the downstream end of the prosthesis), a relatively constant diameter portion. At its proximal portion (at the upstream end of the prosthesis), the endograft system 1000 is able to impart a configuration change to selectively adjustable portion of the implant. Features of the inventive controllable endograft system 1000 are described in further detail in U.S. patent application Ser. No. 11/888,009, filed Jul. 31, 2007, and Ser. No. 12/822,291, filed Jun. 24, 2010, which have been incorporated herein and detail of which is not replicated herein for the sake of brevity.

The exemplary sealable endograft system 1000 shown in FIGS. 1 and 2 comprises a hollow tubular endograft body 1005 having an accommodating proximal cuff 1010 and an intermediate, substantially rigid, tubular member 1015. The distal end of such an endograft (not shown in FIGS. 1 and 2) may be any or all of accommodating, elastic, rigid, stent-laden, or even replicate the proximal end, depending upon the various exemplary embodiments according to the present invention. A selectively adjustable circumferential assembly 1020 is disposed at the proximal cuff 1010. Contained in one exemplary embodiment of the circumferential assembly 1020 is a circumferential channel enclosing an adjustment member 1025 (indicated only diagrammatically with a solid line). The adjustment member 1025 causes the expansion/contraction of the accommodating proximal cuff 1010 by looping around the perimeter and by being lengthened or shortened, respectively. The adjustment member 1025, for example, interacts with a control device 1030 that is operable to cause an increase or decrease in the circumference of the circumferential loop 1025 by the application of rotational torque to the distal aspect of an adjustment tool 1035 emerging from the control device 1030. The adjustment member 1025 can be integral with the adjustment tool 1035 in an exemplary embodiment of the circumferential assembly 1020, or can be removable as shown, for example, in FIG. 10A.

Such an adjustment member 1025 may take many forms in the present invention. In one exemplary embodiment according to the present invention, the adjustment member 1025 is a micro-threaded cable that is fixed at one end to the control device 1030, which is in the form of a microcylinder, and the adjustment tool 1035 threads through a threaded aspect of the microcylinder 1030 in order to effect a change in the circumference of the proximal cuff 1010. A forwardly imposed torque on the adjustment tool 1035 cause expansion of the adjustment tool 1035. Expansion of the adjustment member 1025 in its circumferential extent has the effect of expanding the proximal aspect of the sealable endograft system 1000 to allow for precise sealing of the sealable endograft system 1000 within a recipient blood vessel such as the aorta (not shown in FIG. 1 or 2). Conversely, reverse torque on the adjustment tool 1035 has the effect of decreasing the circumference of the circumferential loop of the adjustment member 1025 and, thus, contracting the proximal aspect of the sealable endograft system 1000, allowing for re-positioning as needed. In FIGS. 1 and 2, the adjustment tool 1035 may extend distally through the lumen of the sealable endograft system 1000. Alternatively, the adjustment tool 1035 may extend distally through a separate lumen provided in the sealable endograft system 1000 (not shown in FIG. 1 or 2).

Figure 4A:
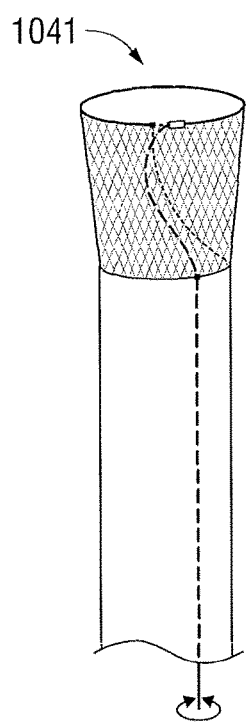
FIG. 4A is a fragmentary, perspective view of the endograft of FIG. 3 with the endograft in a relatively contracted form.
Figure 4B:
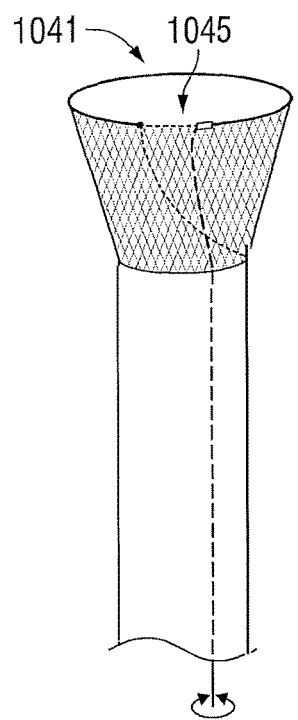
FIG. 4B is a fragmentary, perspective view of the endograft of FIG. 3 with the endograft in a partially expanded form.
Figure 4C:
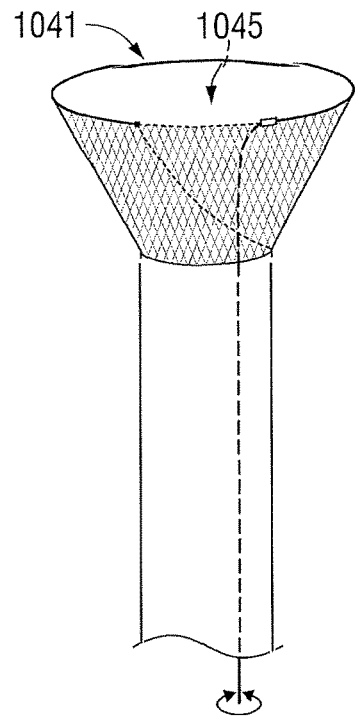
FIG. 4C is a fragmentary, perspective view of the endograft of FIG. 3 with the endograft in a fully expanded form.

FIGS. 3 and 4A to 4C are perspective views of yet another exemplary embodiment of a proximal aspect of a sealable endograft system 1000 according to the present invention that further incorporates a stent or lattice structure 1041 (which, in another embodiment, can be a compressible foam gasket). The lattice structure 1041 is provided with a lattice interruption 1045 to allow for variations in the circumference of the proximal aspect of the endograft. This lattice interruption 1045 may take the form of a V-shape as shown in FIGS. 4B and 4C or may be otherwise configured. As in FIGS. 1 and 2, the sealable endograft system 1000 of FIG. 3 also has an accommodating proximal cuff 1010 which encloses the terminal lattice structure 1040 as shown and also encloses an adjustment member 1025 that loops through a control device 1030 that is provided to allow increase or decrease in the circumference of the, e.g., circumferential loop of the adjustment member 1025 by the application of rotational torque to the distal aspect of the adjustment tool 1035 emerging from the control device 1030. The progression of FIGS. 4A to 4C shows the endograft in a relatively contracted form in FIG. 4A, in a partially expanded form in FIG. 4B, and in a fully expanded form in FIG. 4C. As the lattice interruption 1045 is closed in FIGS. 3 and 44, it can be seen only in FIGS. 4B and 4C. One exemplary configuration for the lattice interruption 1045 can be a woven material that is stretched in the expanded state and attached to the lattice 1041 and, when allowed to reduce, the woven material resist buckling. This configuration allows the diameter to increase beyond the maximum diameter that the graft will allow with the stent alone.

Figure 5A:
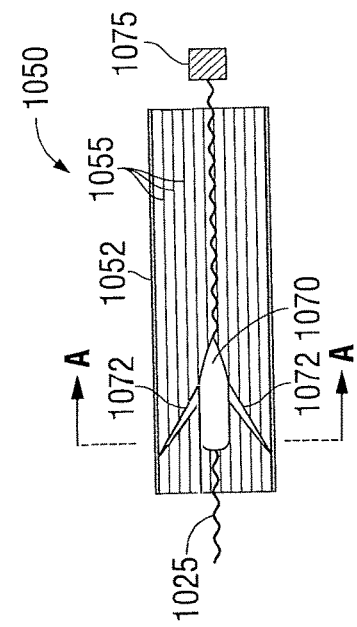
FIG. 5A is a fragmentary, partially hidden, perspective view of an exemplary embodiment of a microcylinder locking mechanism with an associated adjustment tool prior to engagement of the microcylinder locking mechanism by the adjustment tool.
Figure 5B:
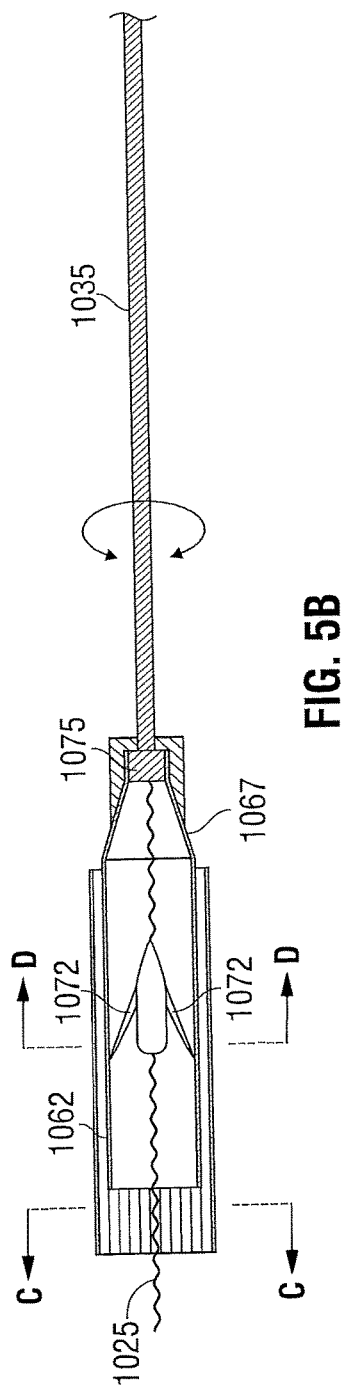
FIG. 5B is a fragmentary, partially hidden, perspective view of the microcylinder locking mechanism and adjustment tool of FIG. 5B with engagement of the microcylinder locking mechanism by the adjustment tool.
Figure 5C:
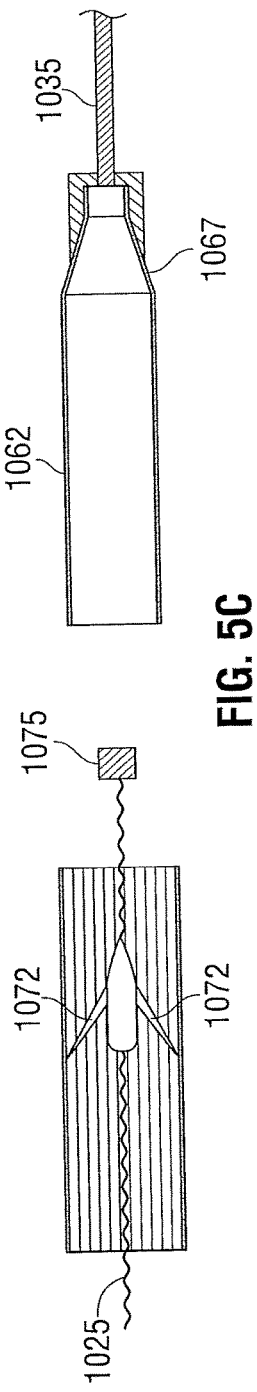
FIG. 5C is a fragmentary, partially hidden, perspective view of an exemplary embodiment of the microcylinder locking mechanism and adjustment tool of FIG. 5B after adjustment and disengagement of the adjustment tool from the microcylinder locking mechanism.

FIG. 5A shows an exemplary embodiment of the control device 1030 in the form of a microcylinder locking mechanism 1050. This locking mechanism 1050 is changed from a locked state to an unlocked state by an adjustment tool 1060, which comprises a tool sheath 1062 having a keyed collar portion 1065. The adjustment tool 1060 is fixed, in both the longitudinal and radial extents, to the remote adjustment tool 1035. The progression of FIGS. 5A to 5C show how the locking mechanism 1050 is changed from the locked state (in which adjustment of the adjustment member 1025 is prohibited) to the unlocked state (in which adjustment of the adjustment member 1025 is permitted), and, then, back to the locked state.

Before explaining the change between states, the configuration of an exemplary embodiment of the locking mechanism 1050 is described further. The exterior of the locking mechanism 1050 is comprised of a microcylinder 1052 having a set of circumferentially spaced-apart, interior striations 1055. The locking mechanism 1050 is longitudinally and rotationally fixed to the proximal cuff 1010. A guide bullet 1070 is received within the hollow, internally striated microcylinder 1052. The guide bullet 1070 has a longitudinal threaded bore that received therein (in a threaded manner) the adjustment member 1025. The adjustment member 1025 completely traverses the bore of the guide bullet 1070 and terminates distally of the guide bullet 1070 in a keyed block 1075 that is rotationally fixed to the adjustment member 1025. The guide bullet 1070 has at least two opposing, flexible tines 1072 that extend radially outward, in a natural state that, together, has a diameter greater than the internal diameter of the locking microcylinder 1052 (the tines can, as well, be spring loaded outwardly). The tines 1072 have a terminal portion that is shaped to fit within a corresponding shaped of each striation 1055 within the microcylinder 1052. As such, when the tines 1072 are compressed and the guide bullet 1070 is placed within the microcylinder with the adjustment member 1025 threaded therewithin, the tines 1072 press outwardly against the internal surface of the microcylinder 1052 and, when appropriately rotated therein, the tines 1072 each lock within a respective opposing one of the striations 1055. In such a state, the tines 1072 both form-fittingly and force-fittingly lock within inner striations 1055 when unconstrained. If, for example, there were three tines 1072 separated by 120 degrees each, then the tines 1072 would each lock within a respective one of the striations 1055 that are, also, 120 degrees apart along the interior surface of the microcylinder 1052. The frictional force of the tines 1072 against the inside surface of the microcylinder 1052 is sufficiently strong to prevent longitudinal movement of the guide bullet 1070, even if the keyed block 1075 is rotated unless the tines 1072 are removed from their locked position against the interior surface of the microcylinder. In such a configuration, the microcylinder 1052 and the guide bullet 1070 prevent rotation of the adjustment member 1025 without, not only a particular external force applied thereto, but also a removal of the tines 1072 from the interior surface of the microcylinder 1052.

Rotation of the adjustment member 1025, therefore, is carried out with the adjustment tool 1060. The adjustment tool 1060 provides both the ability to rotate the keyed block 1075 but also the ability to separate the tines 1072 from the interior surface of the microcylinder 1052. To carry out these functions, the tool sheath 1062 has a sufficient cylindrical length to slide between the tines 1072 and the interior surface of the microcylinder 1052 anywhere the tines 1072 are contacting the interior surface. As such, the longitudinal length of the tool sheath 1062 can be, but does not necessarily have to be, as long as the microcylinder 1052. FIG. 5A shows the microcylinder 1052 with the guide bullet 1070 in a locked position, prior to interface by the remote adjustment tool 1060. When the adjustment tool 1060 is slid into the microcylinder 1052, as shown in the progression of FIGS. 5A to 5B, the smooth interior surface of the tool sheath 1062 first slides along the outer surface of the tines and, then, along and past the distal ends of the tines 1072, at which time the tines 1072 no longer contact the interior surface of the microcylinder 1052. The orientation of the microcylinder locking mechanism 1050 and the adjustment tool 1060 in FIG. 5B now allows for repositioning of the adjustment member 1025 and relocation of the guide bullet 1070 within the microcylinder 1052.

The keyed collar portion 1065 has a distal taper 1067 that reduces the outer diameter of the tool sheath 1062 inwards to such an extent that it acts as a funnel to direct the keyed block 1075 directly into the radial center of the keyed collar portion 1065. At the proximal-most end of the collar portion 1065 is an internal key 1069 having an internal circumferential shape corresponding to an external circumferential shape of the keyed block 1075. As such, when the adjustment tool 1060 is inserted into the microcylinder 1052 and releases the tines 1072 from the interior surface thereof, the tool sheath 1062 can pass the tines 1072 (wherever they may be inside the microcylinder 1052) sufficiently far to permit the keyed block 1075 to slide along the interior distal taper 1067 and press against the internal bore of the key 1069. With slight rotation either way of the adjustment tool 1060 (by rotation of the adjustment tool 1035), the keyed block 1075 will fall into the internal bore of the key 1069 in a form-fit, thereby enabling rotation of the adjustment member 1025 (via keyed block 1075) in a corresponding manner to any rotation of the adjustment tool 1035 by a user.

The locking mechanism 1050 is longitudinally and rotationally fixed to the circumferential assembly 1020 such that rotation of the locking mechanism 1050 in a first direction causes a contraction of the circumferential assembly 1020 and rotation of the locking mechanism 1050 in the opposition direction causes an expansion of the circumferential assembly 1020. As can be seen in FIGS. 5B and 5C, the keyed block 1075 is rotated to cause the guide bullet 1070 to advance towards the keyed block 1075. FIG. 5C shows the microcylinder locking mechanism 1050 with the adjustment tool 1060 after adjustment and disengagement of the microcylinder locking mechanism 1050 by the adjustment tool 1060 with a fixed repositioning of the guide bullet 1070 and a distal lengthening of the adjustment member 1025 with respect to the microcylinder 1052. As the final position of the keyed block 1075 is further away from the microcylinder 1052, and because the microcylinder 1052 is fixed to the control device 1030 of the circumferential assembly 1020, this exemplary movement of the adjustment member 1025 indicates that the circumferential assembly 1020 has reduced in diameter.

Various alternative embodiments of this locking mechanism are envisioned where a number of the individual parts are fixed or moving with respect to other ones of the parts of the circumferential assembly 1020, the control device 1030, the locking mechanism 1050, and/or the adjustment tool 1060. In one alternative embodiment of the microcylinder locking mechanism 1050, the collar portion 1065 of the remote adjustment tool 1060 can contains inner striations (similar to or different from the striations 1055 of the microcylinder 1052) that allow it to capture and turn the guide bullet 1070 through removable fixation of the tines 1072 therein (see FIG. 6E). In such a configuration, the guide bullet 1070 can be fixed rotationally to the adjustment member 1025.

Figure 6D:
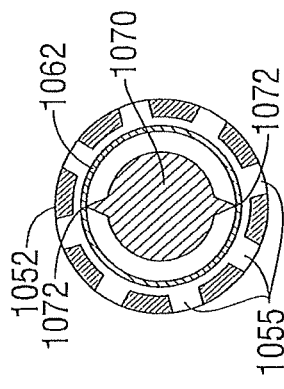
FIG. 6D is an axial cross-sectional view of the microcylinder, the guide bullet, and the tool sheath along section line D-D of FIG. 5B without the adjustment member with the tines removed from the microcylinder by the adjustment tool.
Figure 6C:
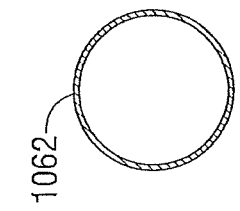
FIG. 6C is an axial cross-sectional view of the microcylinder along section line C-C of FIG. 5B.
Figure 6B:
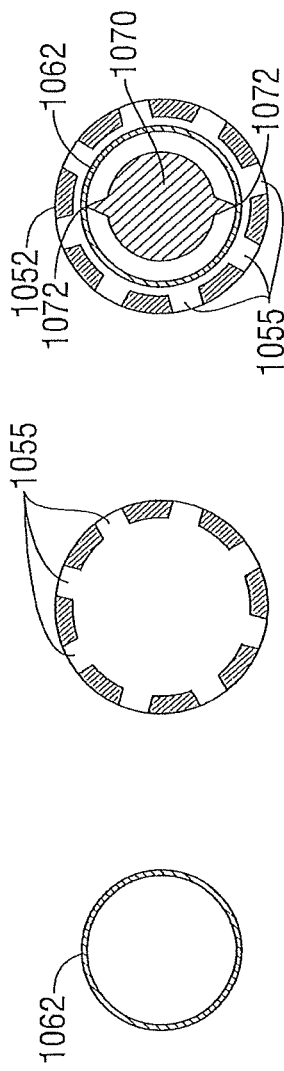
FIG. 6B is an axial cross-sectional view of the adjustment tool along section line B-B of FIG. 5A.
Figure 6A:
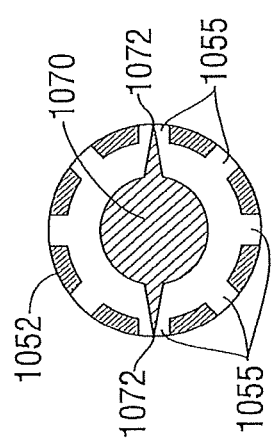
FIG. 6A is an axial cross-sectional view of the microcylinder and guide bullet along section line A-A of FIG. 5A with tines captures in striations of the microcylinder.

The inner striations 1055 of the microcylinder 1052 may be grooves, threads, detents, slots, or other surface features sufficient to allow capture of the tines 1072 upon their release as shown in further detail, for example, in the cross-sections of FIGS. 6A to 6G. FIG. 6A is a cross-section along section line A-A of the microcylinder 1052 and guide bullet 1070 of FIG. 5A, in which the tines 1072 having an exemplary triagonal cross-sectional shape are caught within two striations 1055 having an exemplary rectangular cross-sectional shape. FIG. 6B is a cross-section along section line B-B of the tool sheath 1062 of FIG. 5A and illustrates the relatively smooth outer surface of the tool sheath 1062. FIG. 6C is a cross-section along section line C-C of the microcylinder 1052 of FIG. 5B without the adjustment member 1025 depicted. FIG. 6D is a cross-section along section line D-D of the microcylinder 1052, the guide bullet 1070, and the tool sheath 1062 of FIG. 5B, in which the tool sheath 1062 captures the guide bullet 1070 and collapses the tines 1072, thereby removing the tines 1072 from the striations 1055 of the microcylinder 1052.

Figure 6G:
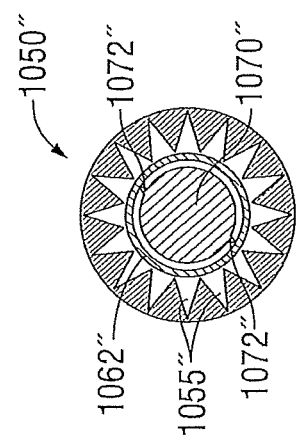
FIG. 6G is an axial cross-sectional view of the microcylinder locking mechanism of FIG. 6F and an adjustment tool according to the invention in which the tines are removed from the microcylinder by the adjustment tool.
Figure 6F:
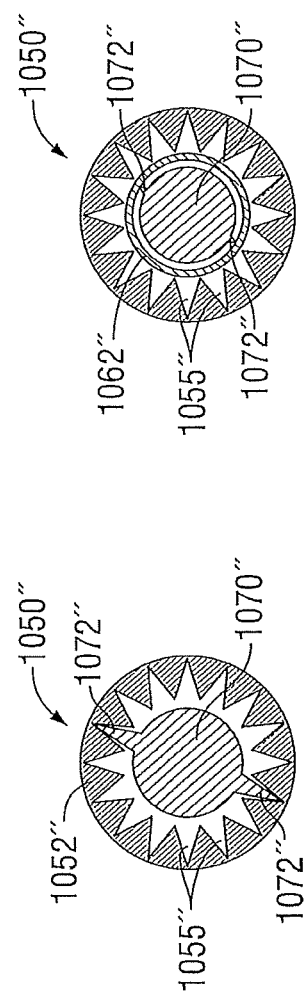
FIG. 6F is an axial cross-sectional view of yet another exemplary embodiment of a microcylinder locking mechanism according to the invention in which the microcylinder has striations with a triangular cross-sectional shape and with the tines caught in the striations of the microcylinder.
Figure 6E:
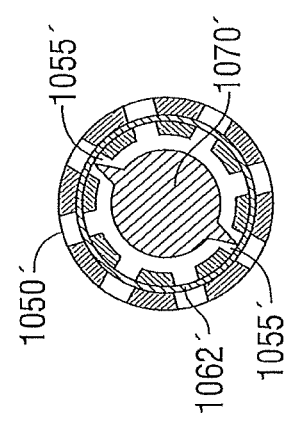
FIG. 6E is an axial cross-sectional view of another exemplary embodiment of a microcylinder locking mechanism and adjustment tool sheath according to the invention where the adjustment tool also has striations having a rectangular cross-sectional shape and has a smooth exterior.

FIG. 6E shows a cross-sectional view of a variation of another exemplary embodiment of the locking mechanism 1050' with the adjustment tool sheath 1062' also having striations 1055' with an exemplary rectangular cross-sectional shape. The tines 1072 are illustrated as expanded within two opposing striations 1055' of the tool sheath 1062'. As the tool sheath 1062' has a smooth exterior, the tool sheath 1062' can rotate without friction within the microcylinder 1052'.

FIGS. 6F and 6G show cross-sectional views of yet another variation of an exemplary embodiment of the microcylinder locking mechanism 1050" and adjustment tool 1060". The locking mechanism 1050" has a microcylinder 1052" with striations 1055" having an exemplary triangular cross-sectional shape. The adjustment tool sheath 1062" has a smooth exterior and interior to slide within the microcylinder 1052" and to slidably capture the tines 1072''', respectively. The tines 1072" are illustrated as expanded within two opposing triangular striations 1055" of the microcylinder 1052" in FIG. 6F and are captured within the tool sheath 1062" in FIG. 6G.

Figure 7A:
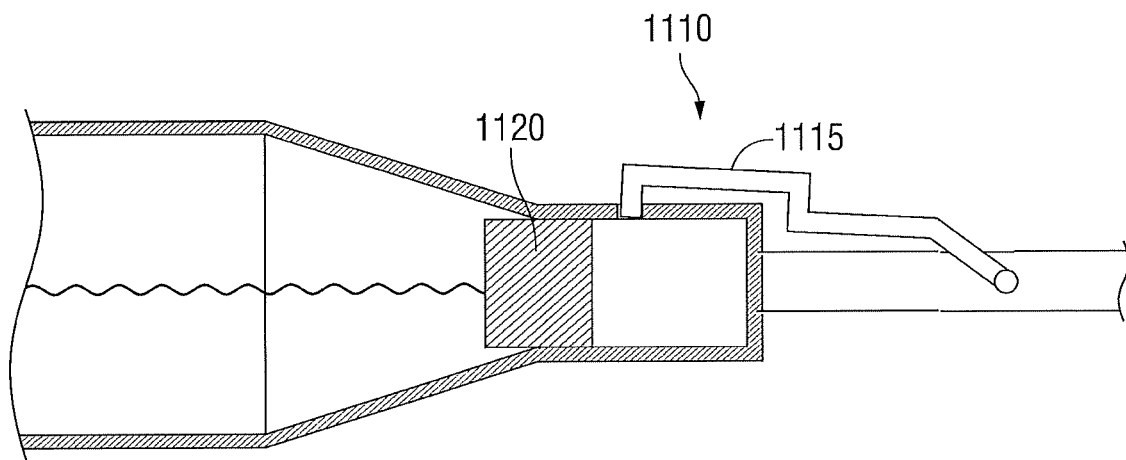
FIG. 7A is a longitudinal, partial cross-sectional view of an exemplary embodiment of an adjustment control locking mechanism according to the present invention with a controllable catch mechanism disengaged.
Figure 7B:
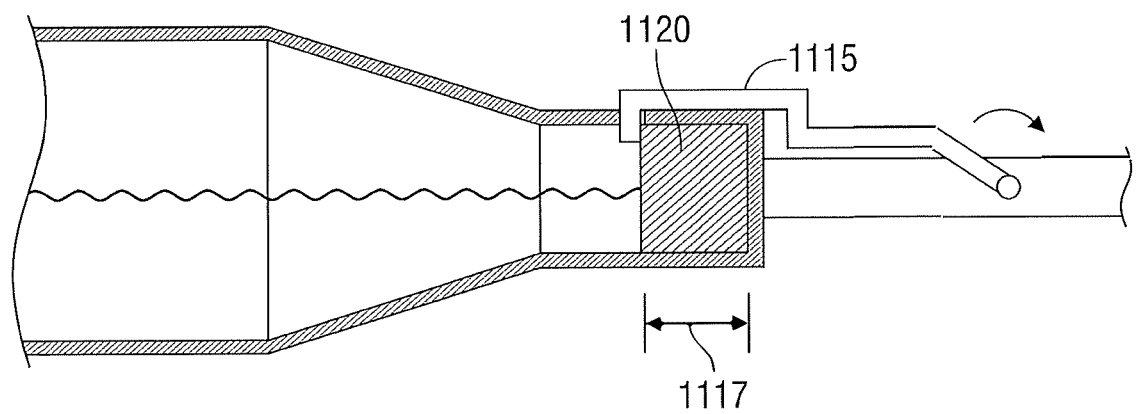
FIG. 7B is a longitudinal, partial cross-sectional view of the adjustment control locking mechanism of FIG. 7A with the controllable catch mechanism engaged.

FIGS. 7A and 7B show longitudinal cross-sectional details of one exemplary embodiment of a locking mechanism 1110 for the adjustment tool 1035 according to the present invention. FIG. 7A shows a locking mechanism 1110 comprising a controllable catch 1115 in a disengaged stated. FIG. 6B shows the locking mechanism 1110 with the controllable catch mechanism 1115 engaged. Once the adjustment member catch 1120 is within the target range 1117 of the locking mechanism, the user can engage a non-illustrated catch deployment device to capture the adjustment member catch 1120.

Figure 8A:
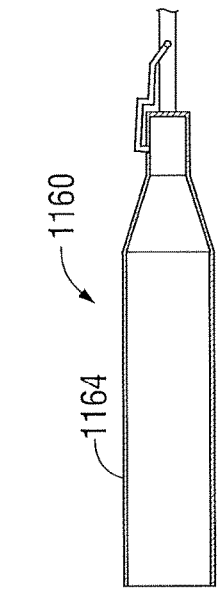
FIG. 8A is a fragmentary, partially hidden, perspective view of an exemplary embodiment of a microcylinder locking mechanism according to the invention with internal locking tines of unequal length and with an associated adjustment tool sheath prior to engagement of the microcylinder locking mechanism by the adjustment tool sheath.
Figure 8B:
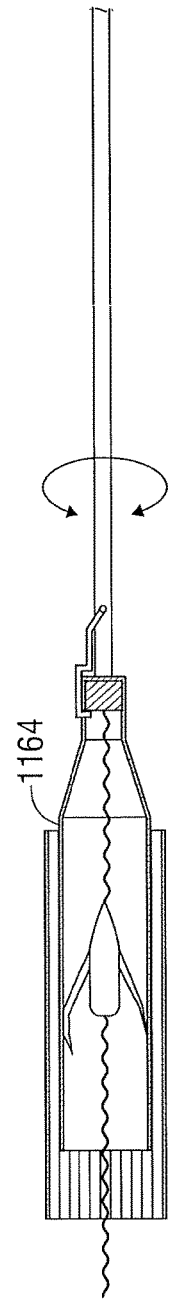
FIG. 8B is a fragmentary, partially hidden, perspective view of the microcylinder locking mechanism and adjustment tool sheath of FIG. 7A with engagement of the microcylinder locking mechanism by the adjustment tool sheath.
Figure 8C:
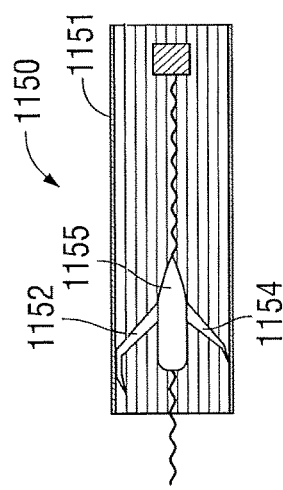
FIG. 8C is a fragmentary, partially hidden, perspective view of the microcylinder locking mechanism and adjustment tool sheath of FIG. 7B after adjustment and disengagement of the microcylinder locking mechanism with the adjustment tool sheath.

FIGS. 8A to 8C show details of still another embodiment of a microcylinder locking mechanism 1150 according to the present invention, in which internal locking tines 1152, 1154 of unequal length are employed to prevent back rotation from torque buildup upon detachment of the remote adjustment tool 1060. FIG. 8A shows the locking mechanism 1150 comprised of a microcylinder 1151 and a guide bullet 1153 with internal locking tines 1152, 1154 of unequal length and an associated adjustment tool 1160 having a tool sheath 1164 prior to engagement of the microcylinder locking mechanism 1150 by the tool sheath 1164. FIG. 8B shows the tool sheath 1164 of FIG. 8A engaged with the microcylinder locking mechanism 1150 to deflect the tines 1152, 1154 away from the interior surface of the microcylinder 1151. FIG. 8C shows the microcylinder locking mechanism 1150 in a locking position different from FIG. 8A after adjustment has occurred and the tool sheath 1164 has been disengaged from the microcylinder 1151.

Figure 9B:
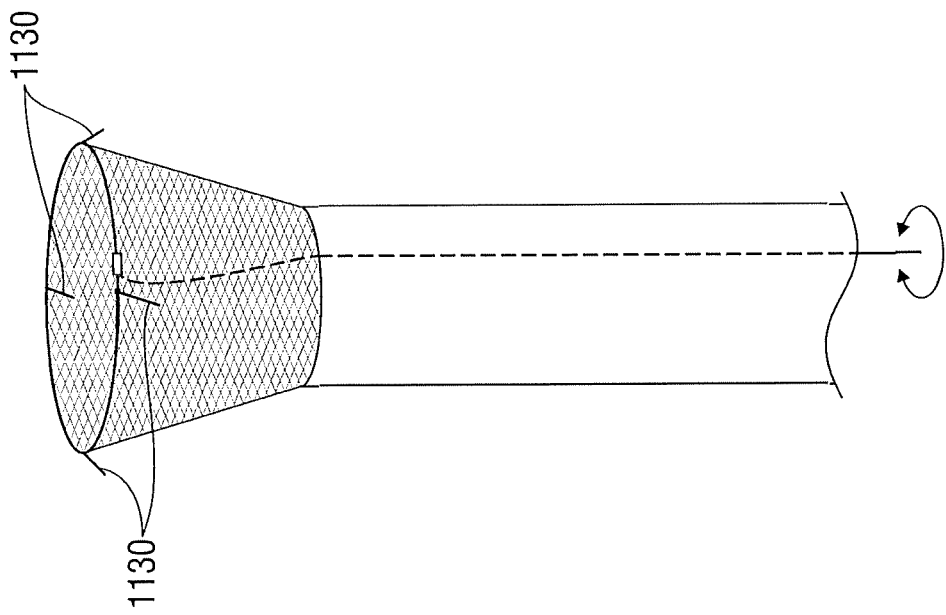
FIG. 9B is a fragmentary, perspective view of the retention tines of FIG. 9A exposed and deployed through a compressible foam gasket exposed by an expanded sealable collar in an exemplary endograft according to the present invention.
Figure 9A:
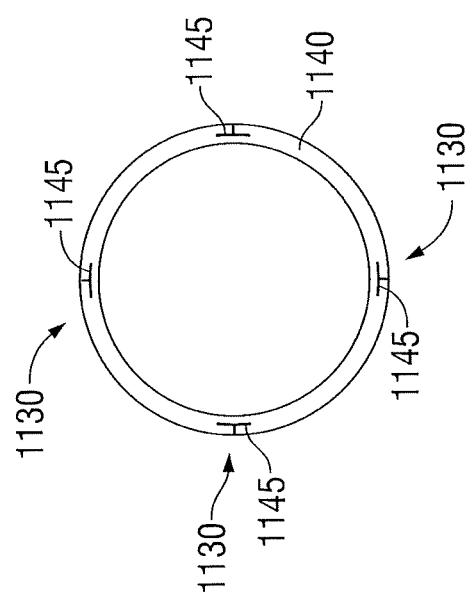
FIG. 9A is an axial cross-sectional view of retention tines sheathed by an expanded compressible foam gasket in an exemplary endograft according to the present invention with the tines in a non-extended state.

FIGS. 9A and 9B show two aspects of details of sheathable retention tines 1130 and a compressible foam sealing gasket 1140 for the proximal terminal aspect of some exemplary embodiments of endografts according to the present invention. FIG. 9A is an axial cross section showing sheathable retention tines 1130 sheathed by an expanded compressible foam gasket 1040 in an exemplary proximal aspect of a sealable endograft system 1000 according to the present invention. FIG. 9B is a perspective view showing sheathable retention tines 1130 exposed and deployed through the compressible foam sealing gasket 1140 disposed at an expanded proximal cuff 1010 in an exemplary endograft according to the present invention. In some exemplary embodiments of the present invention, the direct pressure of the adjustment member 1025 on the footplate 1145 of the tines may be used to extend the sheathable tines 1130 through the compressible foam gasket 1040 and into the wall of a recipient blood vessel. In yet other exemplary embodiments of the present invention, direct pressure of the adjustment member 1025 may exert force on non-illustrated footplate bands that may be attached to or adjacent the footplates 1145 of the tines 1130 and may be used to extend the sheathable tines 1130 through the compressible foam gasket 1040 and into the wall of a recipient blood vessel. Such footplate bands may, themselves, be the base of the sheathable tines 1130 in certain exemplary embodiments of the present invention. Not shown in FIGS. 9A and 9B, the adjustment member 1025 may course though eyelets, other brackets or may otherwise be moveably connected to the footplates 1145 to maintain equal pressure and desired orientation upon expansion of the adjustment member loop.

In the various embodiments of sealable endograft systems according to the present invention, the distal attachment of the endograft to the aortic wall distal to the aneurysm sac may be accomplished in a conventional manner using an expandable lattice component at the distal cuffs, or variations on the adjustable, sealable mechanism disclosed herein may be employed to secure distal seals. The distal seals are subject to lower pressure demands, and the anatomic constraints of sufficient aortic neck distally are generally less problematic than for the proximal seal.

FIGS. 10 to 13 provide anatomic views of another exemplary embodiment of an endograft implant according to the present invention in which the implant is a universal proximal cuff endovascular implant for treatment of an abdominal aortic aneurysm. Endografts with the features shown in the various embodiments of the present invention have unique abilities to accommodate to anatomic variations that would preclude or compromise use of conventional endograft systems. The universal proximal cuff implants of the present invention allow an operator to make use of their ability to securely seal and attach in anatomic sites where conventional endografts cannot be securely placed, and then allow a conventional endograft to securely dock with the universal proximal cuff endovascular implants distally.

Universal proximal cuff endovascular implants of the present invention may be provided with any of the elements disclosed in the present and the incorporated co-pending applications referenced herein. Such elements include, but are not limited to, attachment of radio-opaque monitoring clip assemblies on the outer surfaces of endografts to allow post-implantation monitoring of slippage or endoleak formation by plain radiographs, steerable delivery systems to permit delivery and seal of an endograft in an anatomically angulated or irregular site, and/or auto-accommodation for post-implantation aortic remodeling.

Figure 10A:
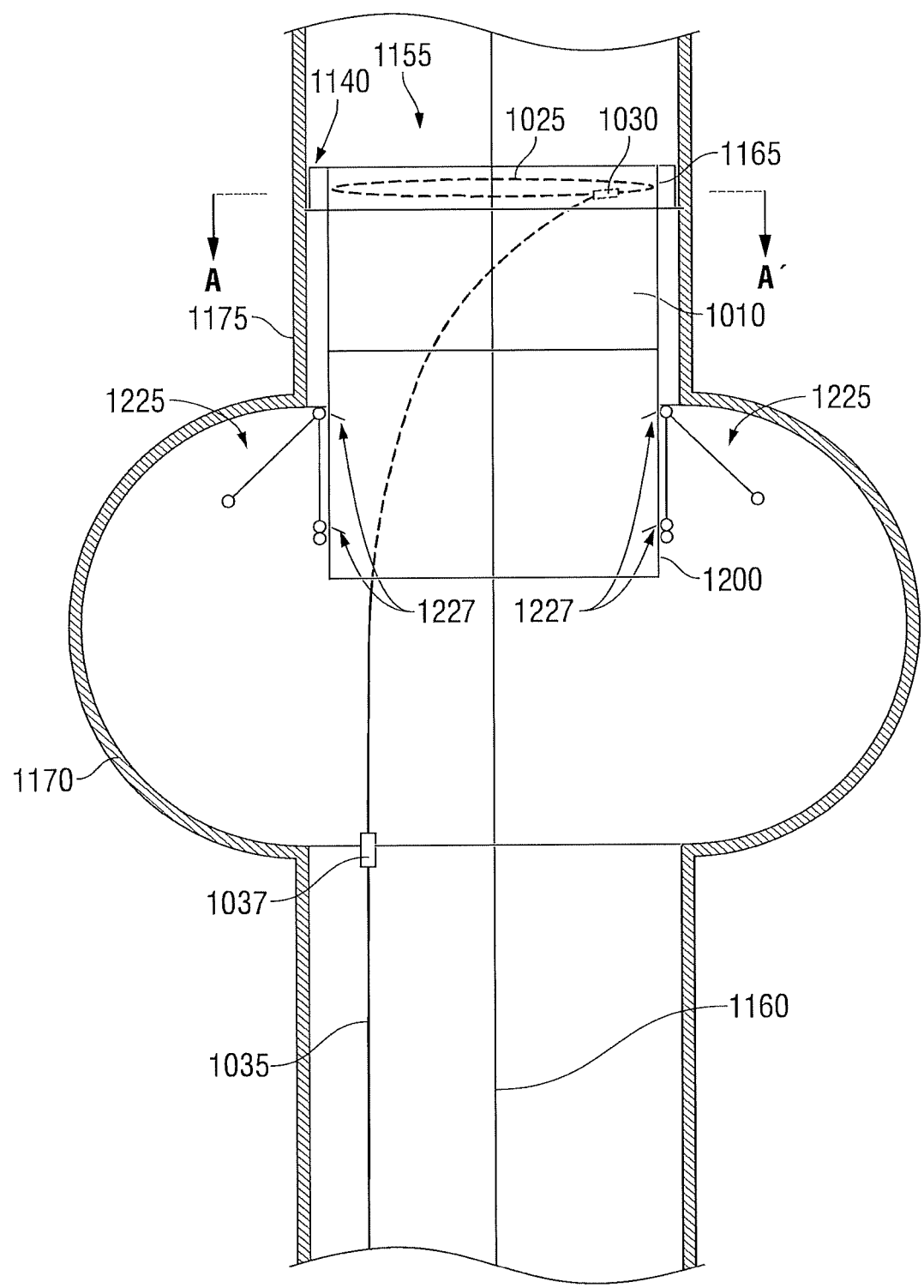
FIG. 10A is a fragmentary, axial cross-sectional view of an exemplary endovascular interface cuff according to the present invention, in which the interface cuff has been positioned over an endovascular guidewire to a desired recipient site in the aorta proximal to an aortic aneurysm sac but has not been expanded therein.
Figure 10B:
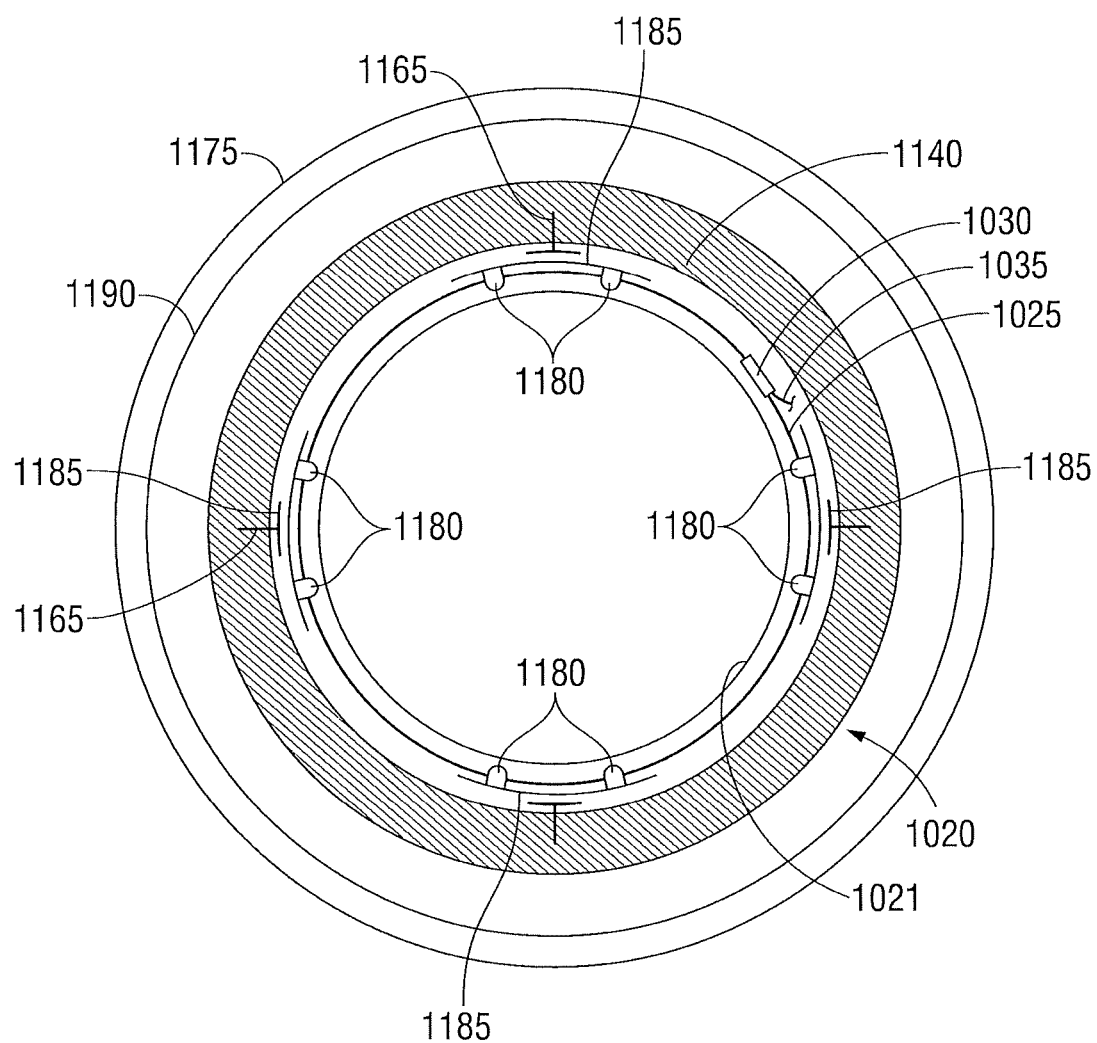
FIG. 10B is a fragmentary, transverse cross-sectional view of the interface cuff of FIG. 10A.

FIG. 10A is an axial cross-sectional view of an exemplary endovascular universal interface cuff 1155 of the present invention to be implanted into an aorta having an aneurysm sac 1170 and an aortic wall 1175. The universal endovascular interface cuff 1155 has been positioned over an endovascular guidewire 1160 to a desired recipient site A-A' proximal to the aortic aneurysm sac 1170. The endovascular universal interface cuff 1155 further comprises an accommodating proximal cuff 1010 and a rigid distal cuff 1200. FIG. 10B provides a transverse cross-sectional view of the exemplary endovascular interface cuff 1155 of FIG. 10A at the level of A-A' in FIG. 10A. In FIGS. 10A and 10B, the compressible foam gasket 1140 is uncompressed and, therefore, covers the retention tines 1165.

In the exemplary embodiment shown in FIG. 10B, the adjustment member 1025 courses in a circumferential loop through eyelets 1180 attached to a series of compression footplates 1185. The compression footplates 1185, among other functions, serve to maintain an orientation of the expanding circumferential loop 1035 in a plane transverse to the aortic lumen 1190, and present a broader pressure contact with the underlying aortic wall 1175 when the circumferential assembly is expanded. The compression footplates 1185 may abut, be attached to, or be contiguous with the retention tines 1165, which are displaced through the compressed compressible foam gasket 1140 and allowed to enter the aortic wall 1175 for overall device stabilization and retention. While four retention tines 1165 and footplates 1185 are shown, this embodiment is merely exemplary and can be any number.

Figure 11A:
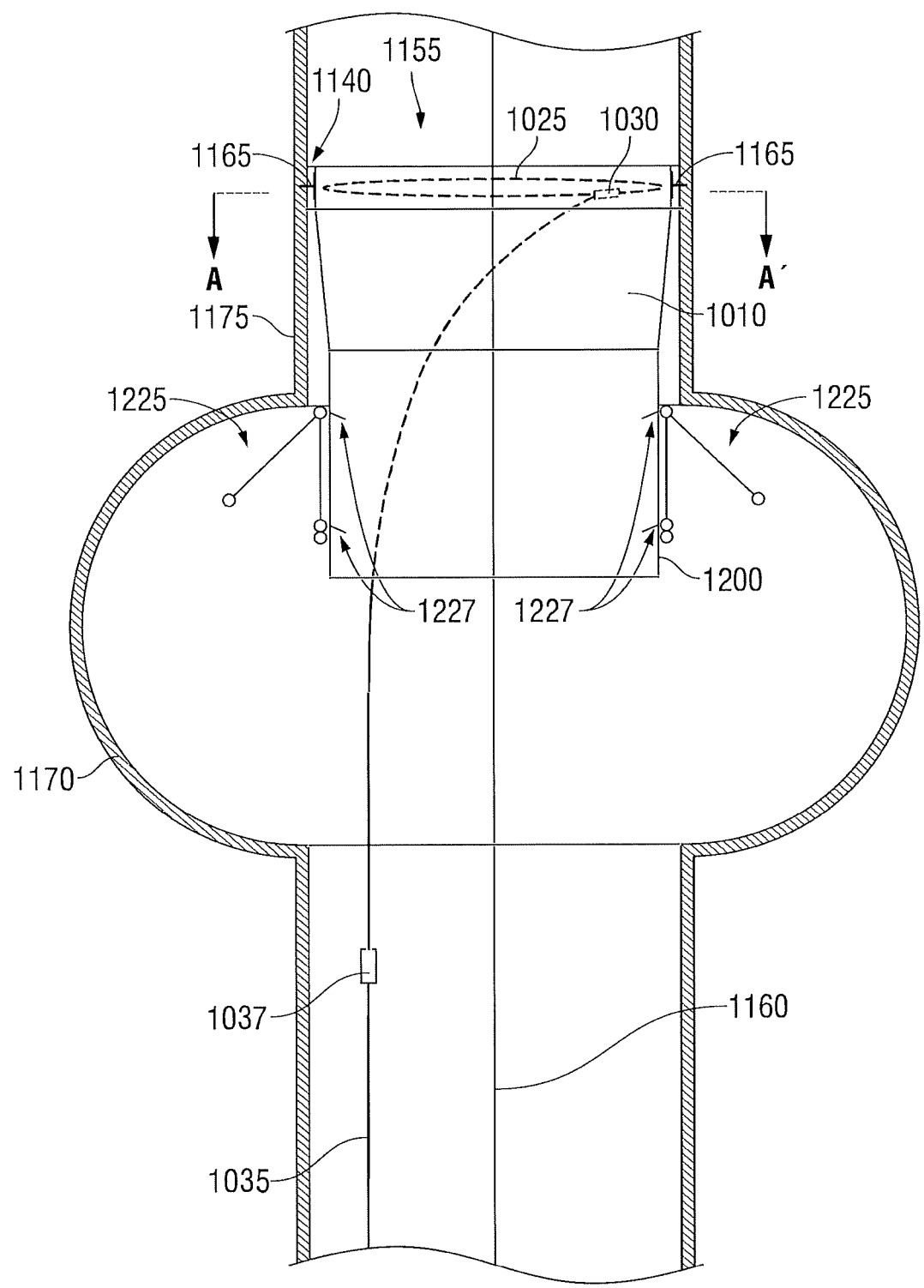
FIG. 11A is a fragmentary, axial cross-sectional view of the interface cuff of FIG. 10A, with expansion of the endovascular interface cuff in the aorta to achieve a seal and with retention tine engagement of the aortic wall in the desired recipient site proximal to the aortic aneurysm sac at the level of A-A'.
Figure 11B:
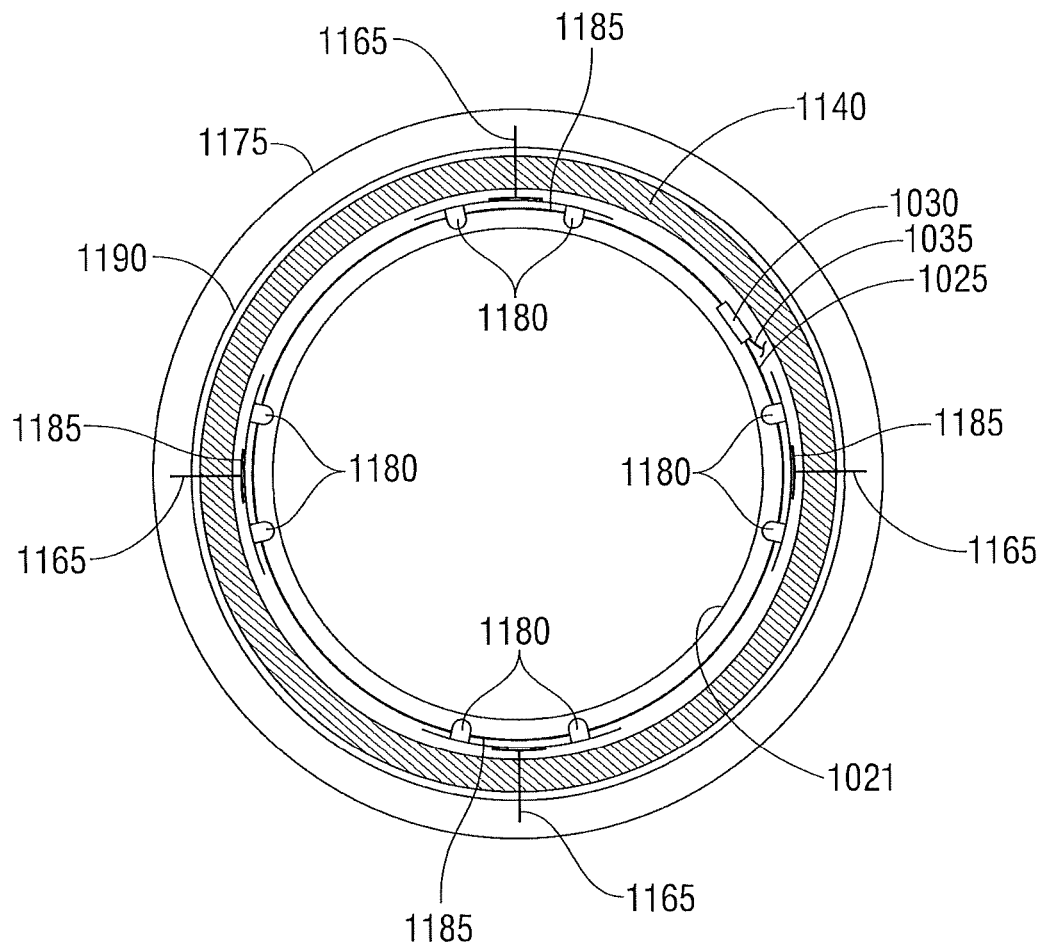
FIG. 11B is a fragmentary, transverse cross-sectional view of the interface cuff of FIG. 11A.

FIG. 11A shows the same axial cross-sectional view of the endovascular universal interface cuff 1155 of FIG. 10A but after the universal endovascular interface cuff 1155 has expanded to achieve a seal in the aortic wall 1175. Due to the expansion of the cuff, the foam gasket 1140 becomes compressed, allowing the retention tines 1165 to protrude radially outward to engage the aortic wall 1175 in the desired recipient site A-A' proximal to the aortic aneurysm sac 1170. In the exemplary embodiment shown in FIG. 11B, the adjustment member 1025 has expanded to move the eyelets 1180 attached to the footplates 1185 outwards. As is evident, the interior lumen of the circumferential assembly 1020 shown in FIG. 11B has increased substantially as compared to the state shown in FIG. 10B. In FIG. 11B, the compression of the foam gasket 1140 and the engagement of the aortic wall 1175 by the retention tines 1165 creates a firm seal between the universal endovascular interface cuff 1155 and the aortic wall 1175.

Figure 12:
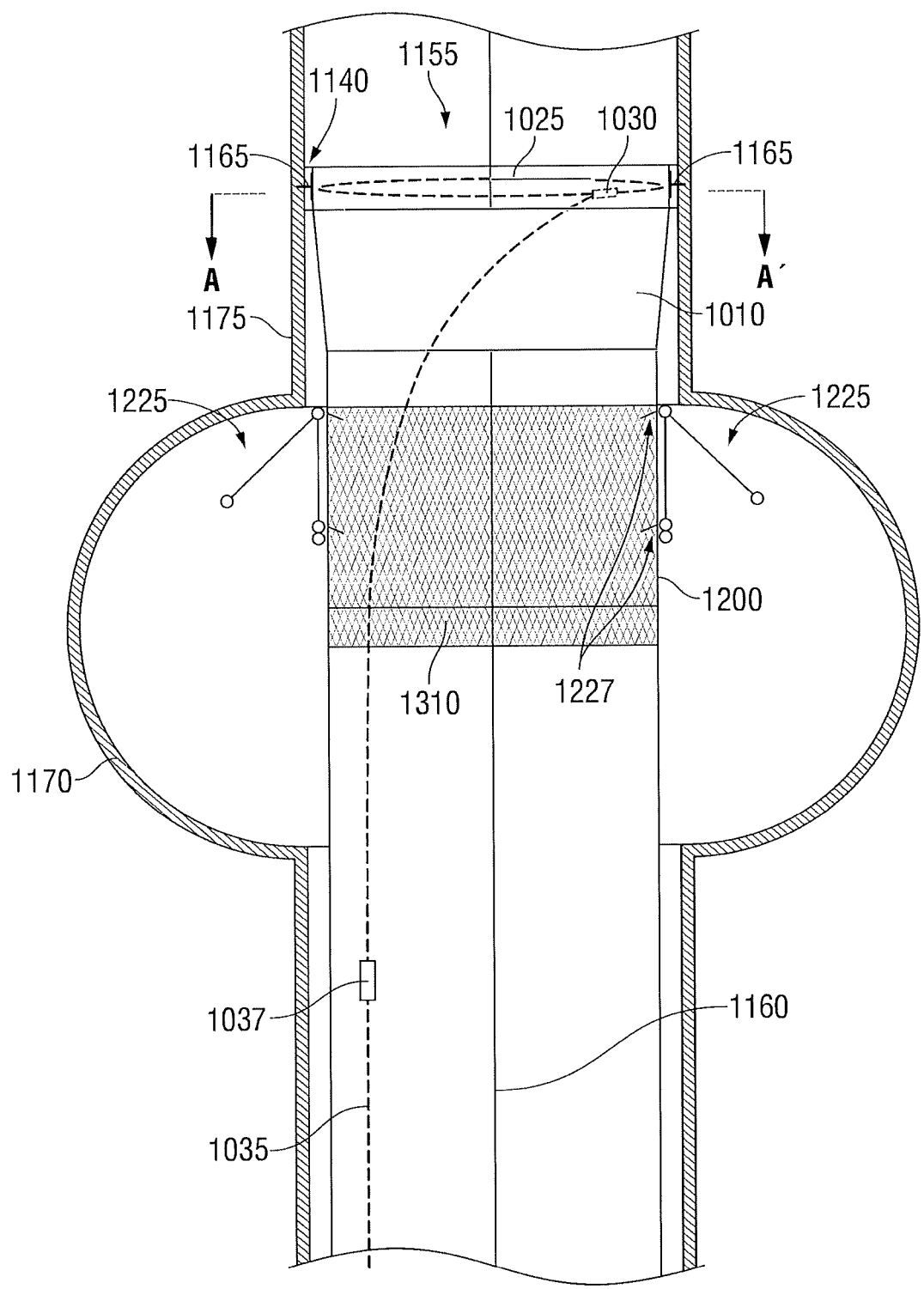
FIG. 12 is a fragmentary, axial cross-sectional view of the interface cuff of FIG. 10A with delivery of an endograft secured within the rigid cuff of the interface cuff.
Figure 13:
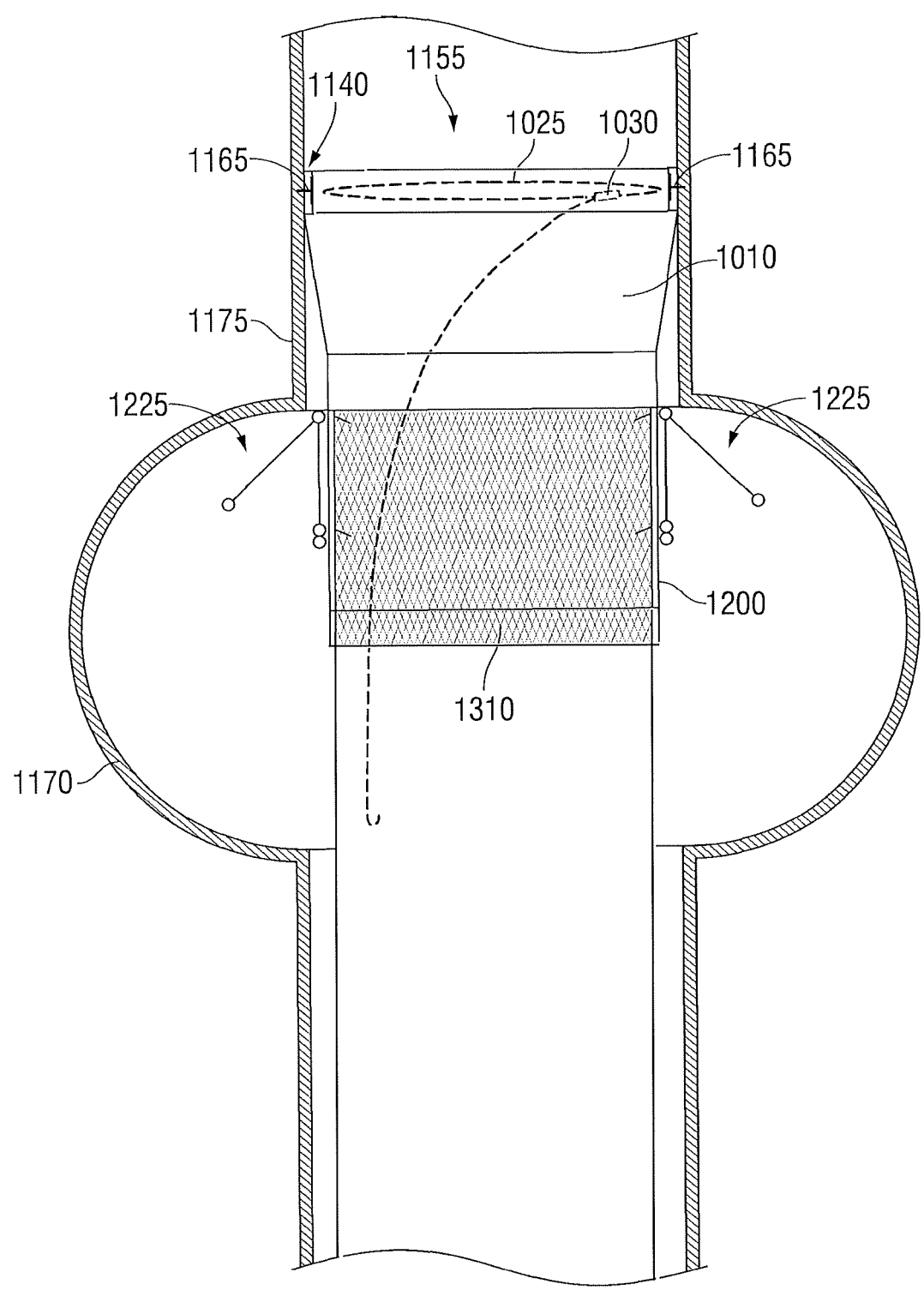
FIG. 13 is a fragmentary, axial cross-sectional view of the interface cuff of FIG. 12 with the guidewire removed and with the adjustment tool detached and removed.

FIG. 12 shows the same axial cross-sectional axial of the universal endovascular interface cuff 1155 of the present invention as in FIGS. 10A and 11A but with delivery of a conventional endograft 1300 into the aortic wall 1175, which endograft 1300 has been secured within the rigid distal cuff 1200 of the universal endovascular interface cuff 1155. The endograft 1300 can include an expandable lattice 1310. FIG. 13 shows the same cross-sectional axial view of an exemplary universal endovascular interface cuff 1155 of the present invention as FIG. 12 but after removal of the endovascular guidewire 1160 and detachment and removal of the adjustment member 1025. Such removal and detachment can be carried out by a release mechanism 1037. The distal attachment of the conventional endograft is not shown in FIGS. 12 and 13, but can be accomplished in the usual manner for conventional endograft implantation sufficient to prevent backfill of the aneurysm sac 1170 from the distal aorta or the iliac vessels.

As shown in FIGS. 10A, 11A, 12, and 13, the rigid distal cuff 1200 includes, at its exterior, exemplary radio-opaque monitoring clip assemblies 1225 to allow post-implantation monitoring of slippage or endoleak formation and/or auto-accommodation for post-implantation aortic remodeling. Likewise, the rigid distal cuff 1200 can be provided with interior graft retention tines 1227 that add to securing, without leaks, the endograft 1300 to the interior of the rigid distal cuff 1200.

The tubular endograft body 1005, the proximal cuff 1010, the rigid distal cuffs 1200, and the endograft body 1300 as described herein may be constructed of solid, woven, non-woven, or mesh materials such as, but not limited to, natural or synthetic rubbers, nylon, GORE-TEX®, elastomers, polyisoprenes, polyphosphazenes, polyurethanes, vinyl plastisols, acrylic polyesters, polyvinylpyrrolidone-polyurethane interpolymers, butadiene rubbers, styrene-butadiene rubbers, rubber lattices, DACRON®, PTFE, malleable metals, other biologically compatible materials or a combination of such biologically compatible materials in a molded, woven, or non-woven configuration, coated, non-coated, and other polymers or materials with suitable resilience and pliability qualities. In certain exemplary embodiments according to the present invention, it is desirable for the non-elastic tubular member 1015 and corresponding structures to be pliable to allow for folding or compressibility without allowing elasticity. In certain exemplary embodiments according to the present invention, it is desirable for the accommodating proximal cuff 1010 and corresponding structures to have plasticity and be compressible or foldable. In any given exemplary embodiment, the non-elastic tubular implant body 1015, the endograft body 1300, the accommodating proximal cuff 1010, and corresponding structures may be constructed of the same material of varying elasticity, or these structures may be constructed of different, but compatible materials.

The adjustment members 1025, the retention tines 1130, 1165, and the microcylinders 1030 and other mechanical components as disclosed herein and in all other embodiments of the present invention may be fabricated of any suitably strong biocompatible material, including, but not limited to titanium, stainless steel, cobalt chromium alloys, other metals, other metal alloys, nitinol, plastics, or ceramics. Similarly, the adjustment members 1025, the retention tines 1130, 1165, and the microcylinders 1030 and other mechanical components may be milled, laser cut, lathed, molded, or extruded.

The compressible foam gaskets 1140 as disclosed herein may be any biocompatible foam material of either an open or closed cell structure with sufficient compressibility and resilience to allow rapid recovery in a non-compressed state. In various exemplary embodiments according to the present invention, such foam materials may be viscoelastic foam with a compressible cellular material that has both elastic (spring-like) and viscous (time-dependent) properties. Viscoelastic foam differs from regular foam by having time-dependent behaviors such as creep, stress relaxation, and hysteresis.

FIGS. 14A and 14B show an alternate exemplary embodiment of a sealable endograft system 2000 according to the present invention in two different states. In the view of FIG. 14A, a hinged lattice structure 2100 is attached to an internal or external surface of at least the proximal portion 2210 of an endograft body 2200 (the "lattice" in these figures is only diagrammatic and is not intended to imply that the only possible number of rings of lattice is greater than one). Either the lattice structure 2100 or the endograft body 2200 can be provided with radially displaced retention tines 2105 that, in a non-distended state of the proximal portion 2210, can be covered within a compressible foam gasket 2300. In the embodiment shown in FIG. 14A, the distal portion 2220 of the endograft body 2200 comprises a non-distensible material and the proximal portion 2210 of the endograft body 2200 is an accommodating cuff comprising a distensible material forming the proximally terminal aspect of the sealable endograft system 2000 and enclosing the terminal hinged lattice structure 2100 therewithin.

A control system 2400 or jack screw shown in FIGS. 14A and 14B is provided to expand and contract the lattice structure 2100. In particular, a torque wire 2410 can be fixed at two points 2420, 2430 longitudinally separate from one another on the lattice structure 2100. This torque wire 2410 has exterior threads that correspond to threaded bores of one of the two points 2420, 2430. Accordingly, when the torque wire 2410 is rotated, the two points 2420, 2430 of the lattice either approach one another (to expand the proximal portion 2210) or retreat from one another (to contract the proximal portion 2210) this imparts motion to all contiguously interconnected lattice elements. It is preferred to have the proximal end point 2430 be bored for rotation but fixed longitudinally. In this case, a smooth-bored collar 2440 is fixed to the wall of the graft 2200, for example, on an interior surface distal of the lattice structure 2100. When the adjustment tool 1035 is rotated, the torque wire 2410 correspondingly rotates to expand or contract the proximal portion 2210 of the endograft 2200. In this manner, in comparison to self-expanding prior art stent structures (e.g., made of nitinol) passively open to their greatest extent when relieved from radially inward compression, the lattice structure of the present invention is able to actively open according to the desire of the user surgeon implanting the prosthesis. As such, the opening performed by prior art self-expanding stent structures in endograft prosthesis are referred to herein as "passive opening" or "passive expansion". In contrast thereto, the expansion performed by the inventive controllable, hinged, lattice structure of the present invention for the disclosed endograft prostheses is referred to herein as "active control" or "active expansion" because it can be actively controlled in both the expansion and contraction directions according to the desire of the user. This is further in contrast to expansion of stent structures using balloon, which case is referred to as "balloon opening" or "balloon expansion" because it occurs only in one direction (expansion) without any ability to contract actively. The single embodiment of the jack screw shown in FIGS. 14A and 14B can be replicated any number of times about the circumference of the lattice structure 2100.

In a non-illustrated alternative to the configuration of the system shown in FIG. 14B, the configuration shown in FIGS. 10A to 11B can be incorporated into the system of FIGS. 14A and 14B to create a hybrid system. The circumferential assembly 1020 can be positioned at the proximal end of the endograft and action of the circumferential loop 1035 within the proximal cuff 1010, can be used to expand and contract the latticework 2100.

Figure 15B:
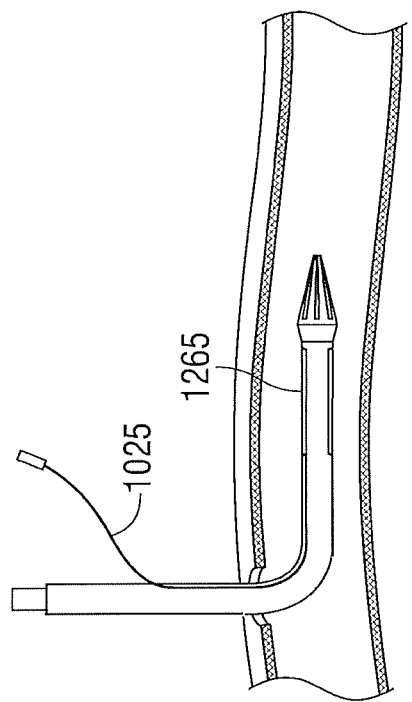
FIG. 15B is a side perspective and partially hidden view of the adjustable vascular cannula of FIG. 15A within a recipient blood vessel with an adjustable seal device in a non-deployed, contracted position.
Figure 15C:
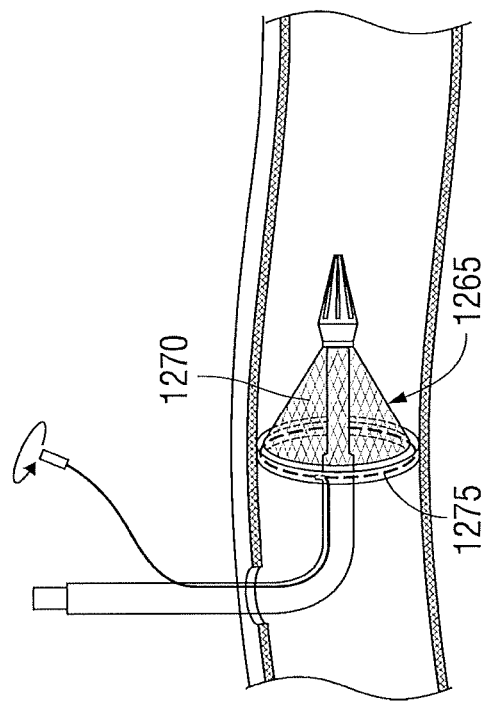
FIG. 15C is a side perspective and partially hidden view of the adjustable vascular cannula of FIG. 15B with the adjustable seal device in a deployed, expanded position.
Figure 15A:
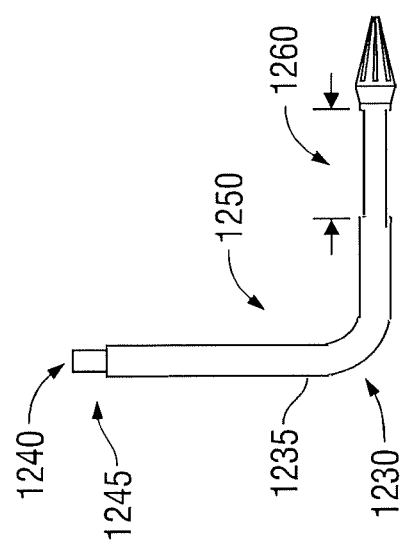
FIG. 15A is a side perspective view of an exemplary embodiment of an adjustable vascular cannula according to the present invention.

FIG. 15A is a lateral view of an exemplary embodiment of an adjustable vascular cannula 1230 according to the present invention. As shown in FIG. 15A, such an adjustable vascular cannula 1230 is a generally tubular structure with external cannula walls 1235 defining a cannula lumen 1240, and comprises a port end 1245, a cannula body 1250, and a cannula tip 1255. As further shown in FIG. 15A, the cannula body 1250 is further provided with a delivery recess 1260 in its external wall structure at or near the junction of the cannula tip 1255. Further still, the adjustable vascular cannula 1230 of FIG. 15A comprises an adjustable seal device 1265 attached to an adjustment member 1025 such as a torque wire that extends beyond the port end 1245 of the adjustable vascular cannula 1230 as shown in FIG. 15B. The adjustment member 1025 may course through the cannula lumen 1240, or it may course through an accessory lumen (not shown in FIG. 15A or 15B) within the cannula wall 1235 substantially parallel to the cannula lumen 1240, or it may course externally to the adjustable vascular cannula 1230 as shown partially within and partially outside the lumen 1240 in FIG. 15B. When in a non-deployed state, as shown in FIG. 15B, the adjustable seal device 1265 is substantially flush with the outer diameter of the cannula walls 1235 within the delivery recess 1260 of the cannula body 1250.

FIG. 15C shows the adjustable seal device 1265 in a deployed state, which is the result of torque applied externally to the adjustment member 1025 by a user. As shown in FIG. 15C, the adjustable seal device 1265 further comprises a hinged adjustable latticework 1270 covered by a sealing cuff 1275 which is constructed of a distensible material. The adjustment member 1025 terminates, for example, in a circumferential loop 1035 within the sealing cuff 1275, where it may be further covered by a compressible foam gasket 1140. The adjustment member 1025 may further pass through a locking mechanism 1050 as disclosed elsewhere herein which serves to regulate the torque applied to the circumferential loop 1035. The hinged adjustable latticework 1270 may further be provided with one or more retention tines 1130, 1165, which are radially displaced from the terminal aspect of the hinged adjustable latticework 1270, and which are enclosed within and covered by the compressible foam gasket 1140 when the adjustable seal device 1265 is not distended. When torque is applied to the adjustment member 1025 by a user, the diameter of the circumferential loop 1035 is increased, displacing the hinged adjustable latticework 1270 as shown in FIG. 15C until the compressible foam gasket 1140 and the sealing cuff 1275 is able to firmly engage the inner wall 1190 of a recipient blood vessel 1175. A slight additional amount of torque applied to the adjustment member 1025 is, then, sufficient to compress the compressible foam gasket 1140 and allow the retention tines 1130, 1165 to engage the wall 1190 of the recipient blood vessel 1175, thus preventing slippage of the cannula during use. In various exemplary embodiments of the present invention, the retention tines 1130, 1165 may be provided to engage the vessel wall 1190 in a substantially straight manner or at angles varying from about 1 degree to about 179 degrees. The retention tines 1130, 1165 may be angled axially or longitudinally in various embodiments according to the present invention. After the use of the cannula is completed, the torque of the adjustment member 1025 may be reversed, collapsing the adjustable seal device 1165, and allowing the compressible foam gasket 1140 to re-expand, thus withdrawing the retention tines 1165 from the vessel wall 1175 and covering the retention tines 1165 to allow atraumatic cannula withdrawal.

Although the foregoing embodiments of the present invention have been described in some detail by way of illustration and example for purposes of clarity and understanding, it will be apparent to those skilled in the art that certain changes and modifications may be practiced within the spirit and scope of the present invention. Therefore, the description and examples presented herein should not be construed to limit the scope of the present invention, the features of which are set forth in the appended claims.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An assembly comprising:
   an implant body comprising a lattice structure, an adjustment member, and a control device, wherein the lattice structure is circumferentially expandable and contractible, wherein the adjustment member and the control device are coupled to the lattice structure, and wherein actuating the adjustment member results in circumferential expansion or contraction of the lattice structure; and
   a delivery apparatus comprising a rotatable adjustment tool and a locking mechanism comprising a controllable catch coupled to an end portion of the rotatable adjustment tool, wherein the rotatable adjustment tool is configured to actuate the adjustment member of the implant body upon rotation of the rotatable adjustment tool, and wherein the controllable catch of the locking mechanism is configured to selectively couple the rotatable adjustment tool to the adjustment member of the implant body.

2. The assembly of claim 1, wherein the controllable catch of the locking mechanism is movable between an engaged configuration and a disengaged configuration, wherein the controllable catch of the locking mechanism engages an adjustment member catch of the adjustment member such that axial movement of the adjustment tool results in corresponding axial movement of the adjustment member when the locking mechanism is in the engaged configuration, and wherein the controllable catch of the locking mechanism disengages the adjustment member catch of the adjustment member such that the rotatable adjustment tool can move axially relative to the adjustment member when the locking mechanism is in the disengaged configuration.

3. The assembly of claim 2, wherein when the controllable catch of the locking mechanism is in the engaged configuration, the controllable catch of the locking mechanism engages the adjustment member catch of the adjustment member such that rotational movement of the adjustment tool results in corresponding rotational movement of the adjustment member relative to the lattice structure, wherein rotating the rotatable adjustment tool in a first direction actuates the adjustment member and radially expands the lattice structure, and wherein rotating the rotatable adjustment tool in a second direction actuates the adjustment member and radially contracts the lattice structure.

4. The assembly of claim 1, wherein the adjustment member is a micro-threaded cable.

5. The assembly of claim 4, wherein the control device is a microcylinder comprising a threaded aspect configured to receive the adjustment member.

6. The assembly of claim 1, wherein the adjustment member comprises a jack screw.

7. The assembly of claim 1, wherein the adjustment member comprises a plurality of jack screws distributed circumferentially around the lattice structure.

8. An assembly comprising:
   a lattice structure, wherein the lattice structure is circumferentially expandable and contractible;
   a torque wire, wherein the torque wire is coupled to the lattice structure at two points longitudinally separate from one another on the lattice structure and configured for circumferentially expanding and contracting the lattice structure;
   an adjustment tool, wherein when the adjustment tool is rotated, the torque wire correspondingly rotates to expand or contract the lattice structure; and
   a smooth-bored collar through which the torque wire extends.

9. The assembly of claim 8, wherein the torque wire has exterior threads that correspond to threaded bores of one of the two points.

10. The assembly of claim 8, wherein when the torque wire is rotated, the two points of the lattice structure either approach one another or retreat from one another.

11. An assembly comprising:
    a radially expandable and contractible stent;
    a jack screw coupled to the stent, wherein rotating the jack screw in a first direction relative to the stent radially expands the stent, and wherein rotating the jack screw in a second direction relative to the stent radially contracts the stent; and
    an adjustment tool configured for rotating the jack screw, wherein the stent has a plurality of bores longitudinally separate from each other, wherein at least one bore of the plurality of bores is a threaded bore with threads that correspond to exterior threads of the jack screw, wherein at least one other bore of the plurality of bores is a non-threaded bore, and wherein the jack screw extends longitudinally through the threaded bore and the non-threaded bore.

12. The assembly of claim 11, wherein the stent is made of nitinol.

13. The assembly of claim 11, wherein the stent is made of a metal alloy.

14. The assembly of claim 11, wherein the stent is made of stainless steel.

15. The assembly of claim 11, wherein the stent is made of cobalt chromium.

16. The assembly of claim 11, further comprising a sealing gasket coupled to the stent.

17. The assembly of claim 16, wherein the sealing gasket is made of a compressible foam.

18. The assembly of claim 17, further comprising a plurality of tine extending through the sealing gasket.

* * * * *